(12) United States Patent
Shuros et al.

(10) Patent No.: US 10,391,319 B2
(45) Date of Patent: Aug. 27, 2019

(54) TRANS SEPTAL IMPLANTABLE MEDICAL DEVICE

(71) Applicant: CARDIAC PACEMAKERS, INC., St. Paul, MN (US)

(72) Inventors: Allan Charles Shuros, St. Paul, MN (US); Christopher A. Hartemink, Shoreview, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 26 days.

(21) Appl. No.: 15/679,757

(22) Filed: Aug. 17, 2017

(65) Prior Publication Data

US 2018/0050208 A1   Feb. 22, 2018

Related U.S. Application Data

(60) Provisional application No. 62/377,204, filed on Aug. 19, 2016.

(51) Int. Cl.

| A61N 1/368 | (2006.01) |
| A61N 1/375 | (2006.01) |
| A61N 1/372 | (2006.01) |
| A61N 1/378 | (2006.01) |
| A61N 1/05  | (2006.01) |

(52) U.S. Cl.
CPC ....... *A61N 1/36843* (2017.08); *A61N 1/0573* (2013.01); *A61N 1/378* (2013.01); *A61N 1/3756* (2013.01); *A61N 1/37229* (2013.01); *A61N 1/37512* (2017.08); *A61N 1/37518* (2017.08); *A61N 2001/058* (2013.01)

(58) Field of Classification Search
CPC ............ A61N 1/36843; A61N 1/37512; A61N 1/17518
See application file for complete search history.

(56) References Cited

U.S. PATENT DOCUMENTS

| 3,835,864 A | 9/1974 | Rasor et al. |
| 3,943,936 A | 3/1976 | Rasor et al. |

(Continued)

FOREIGN PATENT DOCUMENTS

| AU | 2008279789 B2 | 10/2011 |
| AU | 2008329620 B2 | 5/2014 |

(Continued)

OTHER PUBLICATIONS

US 8,886,318 B2, 11/2014, Jacobson et al. (withdrawn)

(Continued)

*Primary Examiner* — Joseph M Dietrich
(74) *Attorney, Agent, or Firm* — Seager, Tufte & Wickhem LLP

(57) ABSTRACT

An implantable medical device (IMD) includes a housing that is configured to be positioned at least in part in a chamber of a heart, and in some cases, in a right ventricle (RV) proximate an RV facing side of the ventricular septum of the heart. When so provided, an RV electrode may be fixed relative to the housing to be proximate the RV facing side of the ventricular septum. An LV electrode may be spaced a distance from the RV electrode and the housing such that the LV electrode is positioned at least partially within the ventricular septum. An LV electrode position adjustment assembly may be used to adjust the depth at which the LV electrode is positioned within the ventricular septum.

20 Claims, 13 Drawing Sheets

(56) References Cited

U.S. PATENT DOCUMENTS

| | | |
|---|---|---|
| 4,142,530 A | 3/1979 | Wittkampf |
| 4,151,513 A | 4/1979 | Menken et al. |
| 4,157,720 A | 6/1979 | Greatbatch |
| RE30,366 E | 8/1980 | Rasor et al. |
| 4,243,045 A | 1/1981 | Maas |
| 4,250,884 A | 2/1981 | Hartlaub et al. |
| 4,256,115 A | 3/1981 | Bilitch |
| 4,263,919 A | 4/1981 | Levin |
| 4,310,000 A | 1/1982 | Lindemans |
| 4,312,354 A | 1/1982 | Walters |
| 4,323,081 A | 4/1982 | Wiebusch |
| 4,357,946 A | 11/1982 | Dutcher et al. |
| 4,365,639 A | 12/1982 | Goldreyer |
| 4,440,173 A | 4/1984 | Hudziak et al. |
| 4,476,868 A | 10/1984 | Thompson |
| 4,522,208 A | 6/1985 | Buffet |
| 4,537,200 A | 8/1985 | Widrow |
| 4,556,063 A | 12/1985 | Thompson et al. |
| 4,562,841 A | 1/1986 | Brockway et al. |
| 4,593,702 A | 6/1986 | Kepski et al. |
| 4,593,955 A | 6/1986 | Leiber |
| 4,630,611 A | 12/1986 | King |
| 4,635,639 A | 1/1987 | Hakala et al. |
| 4,674,508 A | 6/1987 | DeCote |
| 4,712,554 A | 12/1987 | Garson |
| 4,729,376 A | 3/1988 | DeCote |
| 4,754,753 A | 7/1988 | King |
| 4,759,366 A | 7/1988 | Callaghan |
| 4,776,338 A | 10/1988 | Lekholm et al. |
| 4,787,389 A | 11/1988 | Tarjan |
| 4,793,353 A | 12/1988 | Borkan |
| 4,819,662 A | 4/1989 | Heil et al. |
| 4,858,610 A | 8/1989 | Callaghan et al. |
| 4,886,064 A | 12/1989 | Strandberg |
| 4,887,609 A | 12/1989 | Cole |
| 4,928,688 A | 5/1990 | Mower |
| 4,967,746 A | 11/1990 | Vandegriff |
| 4,987,897 A | 1/1991 | Funke |
| 4,989,602 A | 2/1991 | Sholder et al. |
| 5,012,806 A | 5/1991 | De Bellis |
| 5,036,849 A | 8/1991 | Hauck et al. |
| 5,040,534 A | 8/1991 | Mann et al. |
| 5,058,581 A | 10/1991 | Silvian |
| 5,078,134 A | 1/1992 | Heilman et al. |
| 5,109,845 A | 5/1992 | Yuuchi et al. |
| 5,113,859 A | 5/1992 | Funke |
| 5,113,869 A | 5/1992 | Nappholz et al. |
| 5,117,824 A | 6/1992 | Keimel et al. |
| 5,127,401 A | 7/1992 | Grevious et al. |
| 5,133,353 A | 7/1992 | Hauser |
| 5,144,950 A | 9/1992 | Stoop et al. |
| 5,170,784 A | 12/1992 | Ramon et al. |
| 5,179,945 A | 1/1993 | Van Hofwegen et al. |
| 5,193,539 A | 3/1993 | Schulman et al. |
| 5,193,540 A | 3/1993 | Schulman et al. |
| 5,241,961 A | 9/1993 | Henry |
| 5,243,977 A | 9/1993 | Trabucco et al. |
| 5,259,387 A | 11/1993 | DePinto |
| 5,269,326 A | 12/1993 | Verrier |
| 5,284,136 A | 2/1994 | Hauck et al. |
| 5,300,107 A | 4/1994 | Stokes et al. |
| 5,301,677 A | 4/1994 | Hsung |
| 5,305,760 A | 4/1994 | McKown et al. |
| 5,312,439 A | 5/1994 | Loeb |
| 5,313,953 A | 5/1994 | Yomtov et al. |
| 5,314,459 A | 5/1994 | Swanson et al. |
| 5,318,597 A | 6/1994 | Hauck et al. |
| 5,324,316 A | 6/1994 | Schulman et al. |
| 5,331,966 A | 7/1994 | Bennett et al. |
| 5,334,222 A | 8/1994 | Salo et al. |
| 5,342,408 A | 8/1994 | deCoriolis et al. |
| 5,370,667 A | 12/1994 | Alt |
| 5,372,606 A | 12/1994 | Lang et al. |
| 5,376,106 A | 12/1994 | Stahmann et al. |
| 5,383,915 A | 1/1995 | Adams |
| 5,388,578 A | 2/1995 | Yomtov et al. |
| 5,404,877 A | 4/1995 | Nolan et al. |
| 5,405,367 A | 4/1995 | Schulman et al. |
| 5,411,031 A | 5/1995 | Yomtov |
| 5,411,525 A | 5/1995 | Swanson et al. |
| 5,411,535 A | 5/1995 | Fujii et al. |
| 5,456,691 A | 10/1995 | Snell |
| 5,458,622 A | 10/1995 | Alt |
| 5,466,246 A | 11/1995 | Silvian |
| 5,468,254 A | 11/1995 | Hahn et al. |
| 5,472,453 A | 12/1995 | Alt |
| 5,522,866 A | 6/1996 | Fernald |
| 5,540,727 A | 7/1996 | Tockman et al. |
| 5,545,186 A | 8/1996 | Olson et al. |
| 5,545,202 A | 8/1996 | Dahl et al. |
| 5,571,146 A | 11/1996 | Jones et al. |
| 5,591,214 A | 1/1997 | Lu |
| 5,620,466 A | 4/1997 | Haefner et al. |
| 5,634,938 A | 6/1997 | Swanson et al. |
| 5,649,968 A | 7/1997 | Alt et al. |
| 5,662,688 A | 9/1997 | Haefner et al. |
| 5,674,259 A | 10/1997 | Gray |
| 5,683,426 A | 11/1997 | Greenhut et al. |
| 5,683,432 A | 11/1997 | Goedeke et al. |
| 5,706,823 A | 1/1998 | Wodlinger |
| 5,709,215 A | 1/1998 | Perttu et al. |
| 5,720,770 A | 2/1998 | Nappholz et al. |
| 5,728,154 A | 3/1998 | Crossett et al. |
| 5,741,314 A | 4/1998 | Daly et al. |
| 5,741,315 A | 4/1998 | Lee et al. |
| 5,752,976 A | 5/1998 | Duffin et al. |
| 5,752,977 A | 5/1998 | Grevious et al. |
| 5,755,736 A | 5/1998 | Gillberg et al. |
| 5,759,199 A | 6/1998 | Snell et al. |
| 5,774,501 A | 6/1998 | Halpern et al. |
| 5,792,195 A | 8/1998 | Carlson et al. |
| 5,792,202 A | 8/1998 | Rueter |
| 5,792,203 A | 8/1998 | Schroeppel |
| 5,792,205 A | 8/1998 | Alt et al. |
| 5,792,208 A | 8/1998 | Gray |
| 5,814,089 A | 9/1998 | Stokes et al. |
| 5,827,216 A | 10/1998 | Igo et al. |
| 5,836,985 A | 11/1998 | Rostami et al. |
| 5,836,987 A | 11/1998 | Baumann et al. |
| 5,842,977 A | 12/1998 | Lesho et al. |
| 5,855,593 A | 1/1999 | Olson et al. |
| 5,873,894 A | 2/1999 | Vandegriff et al. |
| 5,891,184 A | 4/1999 | Lee et al. |
| 5,897,586 A | 4/1999 | Molina |
| 5,899,876 A | 5/1999 | Flower |
| 5,899,928 A | 5/1999 | Sholder et al. |
| 5,919,214 A | 7/1999 | Ciciarelli et al. |
| 5,935,078 A | 8/1999 | Feierbach |
| 5,941,906 A | 8/1999 | Barreras, Sr. et al. |
| 5,944,744 A | 8/1999 | Paul et al. |
| 5,954,757 A | 9/1999 | Gray |
| 5,978,713 A | 11/1999 | Prutchi et al. |
| 5,991,660 A | 11/1999 | Goyal |
| 5,991,661 A | 11/1999 | Park et al. |
| 5,999,848 A | 12/1999 | Gord et al. |
| 5,999,857 A | 12/1999 | Weijand et al. |
| 6,016,445 A | 1/2000 | Baura |
| 6,026,320 A | 2/2000 | Carlson et al. |
| 6,029,085 A | 2/2000 | Olson et al. |
| 6,041,250 A | 3/2000 | DePinto |
| 6,044,298 A | 3/2000 | Salo et al. |
| 6,044,300 A | 3/2000 | Gray |
| 6,055,454 A | 4/2000 | Heemels |
| 6,073,050 A | 6/2000 | Griffith |
| 6,076,016 A | 6/2000 | Feierbach |
| 6,077,236 A | 6/2000 | Cunningham |
| 6,080,187 A | 6/2000 | Alt et al. |
| 6,083,248 A | 7/2000 | Thompson |
| 6,106,551 A | 8/2000 | Crossett et al. |
| 6,115,636 A | 9/2000 | Ryan |
| 6,128,526 A | 10/2000 | Stadler et al. |
| 6,141,581 A | 10/2000 | Olson et al. |
| 6,141,588 A | 10/2000 | Cox et al. |
| 6,141,592 A | 10/2000 | Pauly |

(56) References Cited

U.S. PATENT DOCUMENTS

| | | | |
|---|---|---|---|
| 6,144,879 A | 11/2000 | Gray | |
| 6,162,195 A | 12/2000 | Igo et al. | |
| 6,164,284 A | 12/2000 | Schulman et al. | |
| 6,167,310 A | 12/2000 | Grevious | |
| 6,201,993 B1 | 3/2001 | Kruse et al. | |
| 6,208,894 B1 | 3/2001 | Schulman et al. | |
| 6,211,799 B1 | 4/2001 | Post et al. | |
| 6,221,011 B1 | 4/2001 | Bardy | |
| 6,240,316 B1 | 5/2001 | Richmond et al. | |
| 6,240,317 B1 | 5/2001 | Villaseca et al. | |
| 6,256,534 B1 | 7/2001 | Dahl | |
| 6,259,947 B1 | 7/2001 | Olson et al. | |
| 6,266,558 B1 | 7/2001 | Gozani et al. | |
| 6,266,567 B1 | 7/2001 | Ishikawa et al. | |
| 6,270,457 B1 | 8/2001 | Bardy | |
| 6,272,377 B1 | 8/2001 | Sweeney et al. | |
| 6,273,856 B1 | 8/2001 | Sun et al. | |
| 6,277,072 B1 | 8/2001 | Bardy | |
| 6,280,380 B1 | 8/2001 | Bardy | |
| 6,285,907 B1 | 9/2001 | Kramer et al. | |
| 6,292,698 B1 | 9/2001 | Duffin et al. | |
| 6,295,473 B1 | 9/2001 | Rosar | |
| 6,297,943 B1 | 10/2001 | Carson | |
| 6,298,271 B1 | 10/2001 | Weijand | |
| 6,307,751 B1 | 10/2001 | Bodony et al. | |
| 6,312,378 B1 | 11/2001 | Bardy | |
| 6,315,721 B2 | 11/2001 | Schulman et al. | |
| 6,336,903 B1 | 1/2002 | Bardy | |
| 6,345,202 B2 | 2/2002 | Richmond et al. | |
| 6,351,667 B1 | 2/2002 | Godie | |
| 6,351,669 B1 | 2/2002 | Hartley et al. | |
| 6,353,759 B1 | 3/2002 | Hartley et al. | |
| 6,358,203 B2 | 3/2002 | Bardy | |
| 6,361,780 B1 | 3/2002 | Ley et al. | |
| 6,368,284 B1 | 4/2002 | Bardy | |
| 6,371,922 B1 | 4/2002 | Baumann et al. | |
| 6,398,728 B1 | 6/2002 | Bardy | |
| 6,400,982 B2 | 6/2002 | Sweeney et al. | |
| 6,400,990 B1 | 6/2002 | Silvian | |
| 6,408,208 B1 | 6/2002 | Sun | |
| 6,409,674 B1 | 6/2002 | Brockway et al. | |
| 6,411,848 B2 | 6/2002 | Kramer et al. | |
| 6,424,865 B1 | 7/2002 | Ding | |
| 6,434,429 B1 | 8/2002 | Kraus et al. | |
| 6,438,410 B2 | 8/2002 | Hsu et al. | |
| 6,438,417 B1 | 8/2002 | Rockwell et al. | |
| 6,438,421 B1 | 8/2002 | Stahmann et al. | |
| 6,440,066 B1 | 8/2002 | Bardy | |
| 6,441,747 B1 | 8/2002 | Khair et al. | |
| 6,442,426 B1 | 8/2002 | Kroll | |
| 6,442,432 B2 | 8/2002 | Lee | |
| 6,443,891 B1 | 9/2002 | Grevious | |
| 6,445,953 B1 | 9/2002 | Bulkes et al. | |
| 6,453,200 B1 | 9/2002 | Koslar | |
| 6,459,929 B1 | 10/2002 | Hopper et al. | |
| 6,470,215 B1 | 10/2002 | Kraus et al. | |
| 6,471,645 B1 | 10/2002 | Warkentin et al. | |
| 6,480,745 B2 | 11/2002 | Nelson et al. | |
| 6,487,443 B2 | 11/2002 | Olson et al. | |
| 6,490,487 B1 | 12/2002 | Kraus et al. | |
| 6,498,951 B1 | 12/2002 | Larson et al. | |
| 6,507,755 B1 | 1/2003 | Gozani et al. | |
| 6,507,759 B1 | 1/2003 | Prutchi et al. | |
| 6,512,940 B1 | 1/2003 | Brabec et al. | |
| 6,522,915 B1 | 2/2003 | Ceballos et al. | |
| 6,526,311 B2 | 2/2003 | Begemann | |
| 6,539,253 B2 | 3/2003 | Thompson et al. | |
| 6,542,775 B2 | 4/2003 | Ding et al. | |
| 6,553,258 B2 | 4/2003 | Stahmann et al. | |
| 6,561,975 B1 | 5/2003 | Pool et al. | |
| 6,564,807 B1 | 5/2003 | Schulman et al. | |
| 6,574,506 B2 | 6/2003 | Kramer et al. | |
| 6,584,351 B1 | 6/2003 | Ekwall | |
| 6,584,352 B2 | 6/2003 | Combs et al. | |
| 6,597,948 B1 | 7/2003 | Rockwell et al. | |
| 6,597,951 B2 | 7/2003 | Kramer et al. | |
| 6,622,046 B2 | 9/2003 | Fraley et al. | |
| 6,628,985 B2 | 9/2003 | Sweeney et al. | |
| 6,647,292 B1 | 11/2003 | Bardy et al. | |
| 6,666,844 B1 | 12/2003 | Igo et al. | |
| 6,689,117 B2 | 2/2004 | Sweeney et al. | |
| 6,690,959 B2 | 2/2004 | Thompson | |
| 6,694,189 B2 | 2/2004 | Begemann | |
| 6,704,602 B2 | 3/2004 | Berg et al. | |
| 6,718,212 B2 | 4/2004 | Parry et al. | |
| 6,721,597 B1 | 4/2004 | Bardy et al. | |
| 6,738,670 B1 | 5/2004 | Almendinger et al. | |
| 6,746,797 B2 | 6/2004 | Benson et al. | |
| 6,749,566 B2 | 6/2004 | Russ | |
| 6,758,810 B2 | 7/2004 | Lebel et al. | |
| 6,763,269 B2 | 7/2004 | Cox | |
| 6,778,860 B2 | 8/2004 | Ostroff et al. | |
| 6,788,971 B1 | 9/2004 | Sloman et al. | |
| 6,788,974 B2 | 9/2004 | Bardy et al. | |
| 6,804,558 B2 | 10/2004 | Haller et al. | |
| 6,807,442 B1 | 10/2004 | Myklebust et al. | |
| 6,847,844 B2 | 1/2005 | Sun et al. | |
| 6,871,095 B2 | 3/2005 | Stahmann et al. | |
| 6,878,112 B2 | 4/2005 | Linberg et al. | |
| 6,885,889 B2 | 4/2005 | Chinchoy | |
| 6,892,094 B2 | 5/2005 | Ousdigian et al. | |
| 6,897,788 B2 | 5/2005 | Khair et al. | |
| 6,904,315 B2 | 6/2005 | Panken et al. | |
| 6,922,592 B2 | 7/2005 | Thompson et al. | |
| 6,931,282 B2 | 8/2005 | Esler | |
| 6,934,585 B1 | 8/2005 | Schloss et al. | |
| 6,957,107 B2 | 10/2005 | Rogers et al. | |
| 6,978,176 B2 | 12/2005 | Lattouf | |
| 6,985,773 B2 | 1/2006 | Von Arx et al. | |
| 6,990,375 B2 | 1/2006 | Kloss et al. | |
| 7,001,366 B2 | 2/2006 | Ballard | |
| 7,003,350 B2 | 2/2006 | Denker et al. | |
| 7,006,864 B2 | 2/2006 | Echt et al. | |
| 7,013,178 B2 | 3/2006 | Reinke et al. | |
| 7,027,871 B2 | 4/2006 | Burnes et al. | |
| 7,050,849 B2 | 5/2006 | Echt et al. | |
| 7,060,031 B2 | 6/2006 | Webb et al. | |
| 7,063,693 B2 | 6/2006 | Guenst | |
| 7,082,336 B2 | 7/2006 | Ransbury et al. | |
| 7,085,606 B2 | 8/2006 | Flach et al. | |
| 7,092,758 B2 | 8/2006 | Sun et al. | |
| 7,110,824 B2 | 9/2006 | Amundson et al. | |
| 7,120,504 B2 | 10/2006 | Osypka | |
| 7,130,681 B2 | 10/2006 | Gebhardt et al. | |
| 7,139,613 B2 | 11/2006 | Reinke et al. | |
| 7,142,912 B2 | 11/2006 | Wagner et al. | |
| 7,146,225 B2 | 12/2006 | Guenst et al. | |
| 7,146,226 B2 | 12/2006 | Lau et al. | |
| 7,149,581 B2 | 12/2006 | Goedeke | |
| 7,149,588 B2 | 12/2006 | Lau et al. | |
| 7,158,839 B2 | 1/2007 | Lau | |
| 7,162,307 B2 | 1/2007 | Patrias | |
| 7,164,952 B2 | 1/2007 | Lau et al. | |
| 7,177,700 B1 | 2/2007 | Cox | |
| 7,181,505 B2 | 2/2007 | Haller et al. | |
| 7,184,830 B2 | 2/2007 | Echt et al. | |
| 7,186,214 B2 | 3/2007 | Ness | |
| 7,191,015 B2 | 3/2007 | Lamson et al. | |
| 7,200,437 B1 | 4/2007 | Nabutovsky et al. | |
| 7,200,439 B2 | 4/2007 | Zdeblick et al. | |
| 7,206,423 B1 | 4/2007 | Feng et al. | |
| 7,209,785 B2 | 4/2007 | Kim et al. | |
| 7,209,790 B2 | 4/2007 | Thompson et al. | |
| 7,211,884 B1 | 5/2007 | Davis et al. | |
| 7,212,871 B1 | 5/2007 | Morgan | |
| 7,226,440 B2 | 6/2007 | Gelfand et al. | |
| 7,228,183 B2 | 6/2007 | Sun et al. | |
| 7,236,821 B2 | 6/2007 | Cates et al. | |
| 7,236,829 B1 | 6/2007 | Farazi et al. | |
| 7,254,448 B2 | 8/2007 | Almendinger et al. | |
| 7,260,436 B2 | 8/2007 | Kilgore et al. | |
| 7,270,669 B1 | 9/2007 | Sra | |
| 7,272,448 B1 | 9/2007 | Morgan et al. | |
| 7,277,755 B1 | 10/2007 | Falkenberg et al. | |

(56) References Cited

U.S. PATENT DOCUMENTS

| | | | |
|---|---|---|---|
| 7,280,872 | B1 | 10/2007 | Mosesov et al. |
| 7,288,096 | B2 | 10/2007 | Chin |
| 7,289,847 | B1 | 10/2007 | Gill et al. |
| 7,289,852 | B2 | 10/2007 | Helfinstine et al. |
| 7,289,853 | B1 | 10/2007 | Campbell et al. |
| 7,289,855 | B2 | 10/2007 | Nghiem et al. |
| 7,302,294 | B2 | 11/2007 | Kamath et al. |
| 7,305,266 | B1 | 12/2007 | Kroll |
| 7,310,556 | B2 | 12/2007 | Bulkes |
| 7,319,905 | B1 | 1/2008 | Morgan et al. |
| 7,321,798 | B2 | 1/2008 | Muhlenberg et al. |
| 7,333,853 | B2 | 2/2008 | Mazar et al. |
| 7,336,994 | B2 | 2/2008 | Hettrick et al. |
| 7,347,819 | B2 | 3/2008 | Lebel et al. |
| 7,366,572 | B2 | 4/2008 | Heruth et al. |
| 7,373,207 | B2 | 5/2008 | Lattouf |
| 7,384,403 | B2 | 6/2008 | Sherman |
| 7,386,342 | B1 | 6/2008 | Falkenberg et al. |
| 7,392,090 | B2 | 6/2008 | Sweeney et al. |
| 7,406,105 | B2 | 7/2008 | DelMain et al. |
| 7,406,349 | B2 | 7/2008 | Seeberger et al. |
| 7,410,497 | B2 | 8/2008 | Hastings et al. |
| 7,425,200 | B2 | 9/2008 | Brockway et al. |
| 7,433,739 | B1 | 10/2008 | Salys et al. |
| 7,496,409 | B2 | 2/2009 | Greenhut et al. |
| 7,496,410 | B2 | 2/2009 | Heil |
| 7,502,652 | B2 | 3/2009 | Gaunt et al. |
| 7,512,448 | B2 | 3/2009 | Malick et al. |
| 7,515,969 | B2 | 4/2009 | Tockman et al. |
| 7,526,342 | B2 | 4/2009 | Chin et al. |
| 7,529,589 | B2 | 5/2009 | Williams et al. |
| 7,532,933 | B2 | 5/2009 | Hastings et al. |
| 7,536,222 | B2 | 5/2009 | Bardy et al. |
| 7,536,224 | B2 | 5/2009 | Ritscher et al. |
| 7,539,541 | B2 | 5/2009 | Quiles et al. |
| 7,544,197 | B2 | 6/2009 | Kelsch et al. |
| 7,558,631 | B2 | 7/2009 | Cowan et al. |
| 7,565,195 | B1 | 7/2009 | Kroll et al. |
| 7,584,002 | B2 | 9/2009 | Burnes et al. |
| 7,590,455 | B2 | 9/2009 | Heruth et al. |
| 7,606,621 | B2 | 10/2009 | Brisken et al. |
| 7,610,088 | B2 | 10/2009 | Chinchoy |
| 7,610,092 | B2 | 10/2009 | Cowan et al. |
| 7,610,099 | B2 | 10/2009 | Almendinger et al. |
| 7,610,104 | B2 | 10/2009 | Kaplan et al. |
| 7,616,991 | B2 | 11/2009 | Mann et al. |
| 7,617,001 | B2 | 11/2009 | Penner et al. |
| 7,617,007 | B2 | 11/2009 | Williams et al. |
| 7,630,767 | B1 | 12/2009 | Poore et al. |
| 7,634,313 | B1 | 12/2009 | Kroll et al. |
| 7,637,867 | B2 | 12/2009 | Zdeblick |
| 7,640,060 | B2 | 12/2009 | Zdeblick |
| 7,647,109 | B2 | 1/2010 | Hastings et al. |
| 7,650,186 | B2 | 1/2010 | Hastings et al. |
| 7,657,311 | B2 | 2/2010 | Bardy et al. |
| 7,668,596 | B2 | 2/2010 | Von Arx et al. |
| 7,682,316 | B2 | 3/2010 | Anderson et al. |
| 7,691,047 | B2 | 4/2010 | Ferrari |
| 7,702,392 | B2 | 4/2010 | Echt et al. |
| 7,713,194 | B2 | 5/2010 | Zdeblick |
| 7,713,195 | B2 | 5/2010 | Zdeblick |
| 7,729,783 | B2 | 6/2010 | Michels et al. |
| 7,734,333 | B2 | 6/2010 | Ghanem et al. |
| 7,734,343 | B2 | 6/2010 | Ransbury et al. |
| 7,738,958 | B2 | 6/2010 | Zdeblick et al. |
| 7,738,964 | B2 | 6/2010 | Von Arx et al. |
| 7,742,812 | B2 | 6/2010 | Ghanem et al. |
| 7,742,816 | B2 | 6/2010 | Masoud et al. |
| 7,742,822 | B2 | 6/2010 | Masoud et al. |
| 7,743,151 | B2 | 6/2010 | Vallapureddy et al. |
| 7,747,335 | B2 | 6/2010 | Williams |
| 7,751,881 | B2 | 7/2010 | Cowan et al. |
| 7,758,521 | B2 | 7/2010 | Morris et al. |
| 7,761,150 | B2 | 7/2010 | Ghanem et al. |
| 7,761,164 | B2 | 7/2010 | Verhoef et al. |
| 7,765,001 | B2 | 7/2010 | Echt et al. |
| 7,769,452 | B2 | 8/2010 | Ghanem et al. |
| 7,783,362 | B2 | 8/2010 | Whitehurst et al. |
| 7,792,588 | B2 | 9/2010 | Harding |
| 7,797,059 | B1 | 9/2010 | Bornzin et al. |
| 7,801,596 | B2 | 9/2010 | Fischell et al. |
| 7,809,438 | B2 | 10/2010 | Echt et al. |
| 7,840,281 | B2 | 11/2010 | Kveen et al. |
| 7,844,331 | B2 | 11/2010 | Li et al. |
| 7,844,348 | B2 | 11/2010 | Swoyer et al. |
| 7,846,088 | B2 | 12/2010 | Ness |
| 7,848,815 | B2 | 12/2010 | Brisken et al. |
| 7,848,823 | B2 | 12/2010 | Drasler et al. |
| 7,860,455 | B2 | 12/2010 | Fukumoto et al. |
| 7,871,433 | B2 | 1/2011 | Lattouf |
| 7,877,136 | B1 | 1/2011 | Moffitt et al. |
| 7,877,142 | B2 | 1/2011 | Moaddeb et al. |
| 7,881,786 | B2 | 2/2011 | Jackson |
| 7,881,798 | B2 | 2/2011 | Miesel et al. |
| 7,881,810 | B1 | 2/2011 | Chitre et al. |
| 7,890,173 | B2 | 2/2011 | Brisken et al. |
| 7,890,181 | B2 | 2/2011 | Denzene et al. |
| 7,890,192 | B1 | 2/2011 | Kelsch et al. |
| 7,894,885 | B2 | 2/2011 | Bartal et al. |
| 7,894,894 | B2 | 2/2011 | Stadler et al. |
| 7,894,907 | B2 | 2/2011 | Cowan et al. |
| 7,894,910 | B2 | 2/2011 | Cowan et al. |
| 7,894,915 | B1 | 2/2011 | Chitre et al. |
| 7,899,537 | B1 | 3/2011 | Kroll et al. |
| 7,899,541 | B2 | 3/2011 | Cowan et al. |
| 7,899,542 | B2 | 3/2011 | Cowan et al. |
| 7,899,554 | B2 | 3/2011 | Williams et al. |
| 7,901,360 | B1 | 3/2011 | Yang et al. |
| 7,904,170 | B2 | 3/2011 | Harding |
| 7,907,993 | B2 | 3/2011 | Ghanem et al. |
| 7,920,928 | B1 | 4/2011 | Yang et al. |
| 7,925,343 | B1 | 4/2011 | Min et al. |
| 7,930,022 | B2 | 4/2011 | Zhang et al. |
| 7,930,040 | B1 | 4/2011 | Kelsch et al. |
| 7,937,135 | B2 | 5/2011 | Ghanem et al. |
| 7,937,148 | B2 | 5/2011 | Jacobson |
| 7,937,161 | B2 | 5/2011 | Hastings et al. |
| 7,941,214 | B2 | 5/2011 | Kleckner et al. |
| 7,945,333 | B2 | 5/2011 | Jacobson |
| 7,946,997 | B2 | 5/2011 | Hübinette |
| 7,949,404 | B2 | 5/2011 | Hill |
| 7,949,405 | B2 | 5/2011 | Feher |
| 7,953,486 | B2 | 5/2011 | Daum et al. |
| 7,953,493 | B2 | 5/2011 | Fowler et al. |
| 7,962,202 | B2 | 6/2011 | Bhunia |
| 7,974,702 | B1 | 7/2011 | Fain et al. |
| 7,979,136 | B2 | 7/2011 | Young et al. |
| 7,983,753 | B2 | 7/2011 | Severin |
| 7,991,467 | B2 | 8/2011 | Markowitz et al. |
| 7,991,471 | B2 | 8/2011 | Ghanem et al. |
| 7,996,087 | B2 | 8/2011 | Cowan et al. |
| 8,000,791 | B2 | 8/2011 | Sunagawa et al. |
| 8,000,807 | B2 | 8/2011 | Morris et al. |
| 8,001,975 | B2 | 8/2011 | DiSilvestro et al. |
| 8,002,700 | B2 | 8/2011 | Ferek-Petric et al. |
| 8,010,209 | B2 | 8/2011 | Jacobson |
| 8,019,419 | B1 | 9/2011 | Panescu et al. |
| 8,019,434 | B2 | 9/2011 | Quiles et al. |
| 8,027,727 | B2 | 9/2011 | Freeberg |
| 8,027,729 | B2 | 9/2011 | Sunagawa et al. |
| 8,032,219 | B2 | 10/2011 | Neumann et al. |
| 8,036,743 | B2 | 10/2011 | Savage et al. |
| 8,046,079 | B2 | 10/2011 | Bange et al. |
| 8,046,080 | B2 | 10/2011 | Von Arx et al. |
| 8,050,297 | B2 | 11/2011 | DelMain et al. |
| 8,050,759 | B2 | 11/2011 | Stegemann et al. |
| 8,050,774 | B2 | 11/2011 | Kveen et al. |
| 8,055,345 | B2 | 11/2011 | Li et al. |
| 8,055,350 | B2 | 11/2011 | Roberts |
| 8,060,212 | B1 | 11/2011 | Rios et al. |
| 8,065,018 | B2 | 11/2011 | Haubrich et al. |
| 8,073,542 | B2 | 12/2011 | Doerr |
| 8,078,278 | B2 | 12/2011 | Penner |
| 8,078,283 | B2 | 12/2011 | Cowan et al. |

(56) References Cited

U.S. PATENT DOCUMENTS

| | | |
|---|---|---|
| 8,095,123 B2 | 1/2012 | Gray |
| 8,102,789 B2 | 1/2012 | Rosar et al. |
| 8,103,359 B2 | 1/2012 | Reddy |
| 8,103,361 B2 | 1/2012 | Moser |
| 8,112,148 B2 | 2/2012 | Giftakis et al. |
| 8,114,021 B2 | 2/2012 | Robertson et al. |
| 8,121,680 B2 | 2/2012 | Falkenberg et al. |
| 8,123,684 B2 | 2/2012 | Zdeblick |
| 8,126,545 B2 | 2/2012 | Flach et al. |
| 8,131,334 B2 | 3/2012 | Lu et al. |
| 8,140,161 B2 | 3/2012 | Willerton et al. |
| 8,150,521 B2 | 4/2012 | Crowley et al. |
| 8,160,672 B2 | 4/2012 | Kim et al. |
| 8,160,702 B2 | 4/2012 | Mann et al. |
| 8,160,704 B2 | 4/2012 | Freeberg |
| 8,165,694 B2 | 4/2012 | Carbanaru et al. |
| 8,175,715 B1 | 5/2012 | Cox |
| 8,180,451 B2 | 5/2012 | Hickman et al. |
| 8,185,213 B2 | 5/2012 | Kveen et al. |
| 8,187,161 B2 | 5/2012 | Li et al. |
| 8,195,293 B2 | 6/2012 | Limousin et al. |
| 8,204,595 B2 | 6/2012 | Pianca et al. |
| 8,204,605 B2 | 6/2012 | Hastings et al. |
| 8,209,014 B2 | 6/2012 | Doerr |
| 8,214,043 B2 | 7/2012 | Matos |
| 8,224,244 B2 | 7/2012 | Kim et al. |
| 8,229,556 B2 | 7/2012 | Li |
| 8,233,985 B2 | 7/2012 | Bulkes et al. |
| 8,262,578 B1 | 9/2012 | Bharmi et al. |
| 8,265,748 B2 | 9/2012 | Liu et al. |
| 8,265,757 B2 | 9/2012 | Mass et al. |
| 8,280,521 B2 | 10/2012 | Haubrich et al. |
| 8,285,387 B2 | 10/2012 | Utsi et al. |
| 8,290,598 B2 | 10/2012 | Boon et al. |
| 8,290,600 B2 | 10/2012 | Hastings et al. |
| 8,295,939 B2 | 10/2012 | Jacobson |
| 8,301,254 B2 | 10/2012 | Mosesov et al. |
| 8,315,701 B2 | 11/2012 | Cowan et al. |
| 8,315,708 B2 | 11/2012 | Berthelsdorf et al. |
| 8,321,021 B2 | 11/2012 | Kisker et al. |
| 8,321,036 B2 | 11/2012 | Brockway et al. |
| 8,332,036 B2 | 12/2012 | Hastings et al. |
| 8,335,563 B2 | 12/2012 | Stessman |
| 8,335,568 B2 | 12/2012 | Heruth et al. |
| 8,340,750 B2 | 12/2012 | Prakash et al. |
| 8,340,780 B2 | 12/2012 | Hastings et al. |
| 8,352,025 B2 | 1/2013 | Jacobson |
| 8,352,028 B2 | 1/2013 | Wenger |
| 8,352,038 B2 | 1/2013 | Mao et al. |
| 8,359,098 B2 | 1/2013 | Lund et al. |
| 8,364,261 B2 | 1/2013 | Stubbs et al. |
| 8,364,276 B2 | 1/2013 | Willis |
| 8,369,959 B2 | 2/2013 | Meskens |
| 8,369,962 B2 | 2/2013 | Abrahamson |
| 8,380,320 B2 | 2/2013 | Spital |
| 8,386,051 B2 | 2/2013 | Rys |
| 8,391,981 B2 | 3/2013 | Mosesov |
| 8,391,990 B2 | 3/2013 | Smith et al. |
| 8,406,874 B2 | 3/2013 | Liu et al. |
| 8,406,879 B2 | 3/2013 | Shuros et al. |
| 8,406,886 B2 | 3/2013 | Gaunt et al. |
| 8,412,352 B2 | 4/2013 | Griswold et al. |
| 8,417,340 B2 | 4/2013 | Goossen |
| 8,417,341 B2 | 4/2013 | Freeberg |
| 8,423,149 B2 | 4/2013 | Hennig |
| 8,428,722 B2 | 4/2013 | Verhoef et al. |
| 8,433,402 B2 | 4/2013 | Ruben et al. |
| 8,433,409 B2 | 4/2013 | Johnson et al. |
| 8,433,420 B2 | 4/2013 | Bange et al. |
| 8,447,412 B2 | 5/2013 | Dal Molin et al. |
| 8,452,413 B2 | 5/2013 | Young et al. |
| 8,457,740 B2 | 6/2013 | Osche |
| 8,457,742 B2 | 6/2013 | Jacobson |
| 8,457,744 B2 | 6/2013 | Janzig et al. |
| 8,457,761 B2 | 6/2013 | Wariar |
| 8,478,407 B2 | 7/2013 | Demmer et al. |
| 8,478,408 B2 | 7/2013 | Hastings et al. |
| 8,478,431 B2 | 7/2013 | Griswold et al. |
| 8,494,632 B2 | 7/2013 | Sun et al. |
| 8,504,156 B2 | 8/2013 | Bonner et al. |
| 8,509,910 B2 | 8/2013 | Sowder et al. |
| 8,515,559 B2 | 8/2013 | Roberts et al. |
| 8,525,340 B2 | 9/2013 | Eckhardt et al. |
| 8,527,068 B2 | 9/2013 | Ostroff |
| 8,532,790 B2 | 9/2013 | Griswold |
| 8,538,526 B2 | 9/2013 | Stahmann et al. |
| 8,541,131 B2 | 9/2013 | Lund et al. |
| 8,543,205 B2 | 9/2013 | Ostroff |
| 8,547,248 B2 | 10/2013 | Zdeblick et al. |
| 8,548,605 B2 | 10/2013 | Ollivier |
| 8,554,333 B2 | 10/2013 | Wu et al. |
| 8,565,882 B2 | 10/2013 | Matos |
| 8,565,897 B2 | 10/2013 | Regnier et al. |
| 8,571,678 B2 | 10/2013 | Wang |
| 8,577,327 B2 | 11/2013 | Makdissi et al. |
| 8,588,926 B2 | 11/2013 | Moore et al. |
| 8,612,002 B2 | 12/2013 | Faltys et al. |
| 8,615,310 B2 | 12/2013 | Khairkhahan et al. |
| 8,626,280 B2 | 1/2014 | Allavatam et al. |
| 8,626,294 B2 | 1/2014 | Sheldon et al. |
| 8,634,908 B2 | 1/2014 | Cowan |
| 8,634,912 B2 | 1/2014 | Bornzin et al. |
| 8,634,919 B1 | 1/2014 | Hou et al. |
| 8,639,335 B2 | 1/2014 | Peichel et al. |
| 8,644,934 B2 | 2/2014 | Hastings et al. |
| 8,649,859 B2 | 2/2014 | Smith et al. |
| 8,670,842 B1 | 3/2014 | Bornzin et al. |
| 8,676,319 B2 | 3/2014 | Knoll |
| 8,676,335 B2 | 3/2014 | Katoozi et al. |
| 8,700,173 B2 | 4/2014 | Edlund |
| 8,700,181 B2 | 4/2014 | Bornzin et al. |
| 8,705,599 B2 | 4/2014 | dal Molin et al. |
| 8,718,766 B2 | 5/2014 | Wahlberg |
| 8,718,773 B2 | 5/2014 | Willis et al. |
| 8,725,260 B2 | 5/2014 | Shuros et al. |
| 8,738,133 B2 | 5/2014 | Shuros et al. |
| 8,738,147 B2 | 5/2014 | Hastings et al. |
| 8,744,555 B2 | 6/2014 | Allavatam et al. |
| 8,744,572 B1 | 6/2014 | Greenhut et al. |
| 8,747,314 B2 | 6/2014 | Stahmann et al. |
| 8,755,884 B2 | 6/2014 | Demmer et al. |
| 8,758,365 B2 | 6/2014 | Bonner et al. |
| 8,768,483 B2 | 7/2014 | Schmitt et al. |
| 8,774,572 B2 | 7/2014 | Hamamoto |
| 8,781,605 B2 | 7/2014 | Bornzin et al. |
| 8,788,035 B2 | 7/2014 | Jacobson |
| 8,788,053 B2 | 7/2014 | Jacobson |
| 8,798,740 B2 | 8/2014 | Samade et al. |
| 8,798,745 B2 | 8/2014 | Jacobson |
| 8,798,762 B2 | 8/2014 | Fain et al. |
| 8,798,770 B2 | 8/2014 | Reddy |
| 8,805,505 B1 | 8/2014 | Roberts |
| 8,805,528 B2 | 8/2014 | Corndorf |
| 8,812,109 B2 | 8/2014 | Blomqvist et al. |
| 8,818,504 B2 | 8/2014 | Bodner et al. |
| 8,827,913 B2 | 9/2014 | Havel et al. |
| 8,831,747 B1 | 9/2014 | Min et al. |
| 8,855,789 B2 | 10/2014 | Jacobson |
| 8,868,186 B2 | 10/2014 | Kroll |
| 8,886,339 B2 | 11/2014 | Faltys et al. |
| 8,903,473 B2 | 12/2014 | Rogers et al. |
| 8,903,500 B2 | 12/2014 | Smith et al. |
| 8,903,513 B2 | 12/2014 | Ollivier |
| 8,909,336 B2 | 12/2014 | Navarro-Paredes et al. |
| 8,914,131 B2 | 12/2014 | Bornzin et al. |
| 8,923,795 B2 | 12/2014 | Makdissi et al. |
| 8,923,963 B2 | 12/2014 | Bonner et al. |
| 8,938,300 B2 | 1/2015 | Rosero |
| 8,942,806 B2 | 1/2015 | Sheldon et al. |
| 8,958,892 B2 | 2/2015 | Khairkhahan et al. |
| 8,977,358 B2 | 3/2015 | Ewert et al. |
| 8,989,873 B2 | 3/2015 | Locsin |
| 8,996,109 B2 | 3/2015 | Karst et al. |
| 9,002,467 B2 | 4/2015 | Smith et al. |

(56) References Cited

U.S. PATENT DOCUMENTS

| | | |
|---|---|---|
| 9,008,776 B2 | 4/2015 | Cowan et al. |
| 9,008,777 B2 | 4/2015 | Dianaty et al. |
| 9,014,818 B2 | 4/2015 | Deterre et al. |
| 9,017,341 B2 | 4/2015 | Bornzin et al. |
| 9,020,611 B2 | 4/2015 | Khairkhahan et al. |
| 9,037,262 B2 | 5/2015 | Regnier et al. |
| 9,042,984 B2 | 5/2015 | Demmer et al. |
| 9,072,911 B2 | 7/2015 | Hastings et al. |
| 9,072,913 B2 | 7/2015 | Jacobson |
| 9,155,882 B2 | 10/2015 | Grubac et al. |
| 9,168,372 B2 | 10/2015 | Fain |
| 9,168,380 B1 | 10/2015 | Greenhut et al. |
| 9,168,383 B2 | 10/2015 | Jacobson et al. |
| 9,180,285 B2 | 11/2015 | Moore et al. |
| 9,192,774 B2 | 11/2015 | Jacobson |
| 9,205,225 B2 | 12/2015 | Khairkhahan et al. |
| 9,216,285 B1 | 12/2015 | Boling et al. |
| 9,216,293 B2 | 12/2015 | Berthiaume et al. |
| 9,216,298 B2 | 12/2015 | Jacobson |
| 9,227,077 B2 | 1/2016 | Jacobson |
| 9,238,145 B2 | 1/2016 | Wenzel et al. |
| 9,242,102 B2 | 1/2016 | Khairkhahan et al. |
| 9,242,113 B2 | 1/2016 | Smith et al. |
| 9,248,300 B2 | 2/2016 | Rys et al. |
| 9,265,436 B2 | 2/2016 | Min et al. |
| 9,265,962 B2 | 2/2016 | Dianaty et al. |
| 9,272,155 B2 | 3/2016 | Ostroff |
| 9,278,218 B2 | 3/2016 | Karst et al. |
| 9,278,229 B1 | 3/2016 | Reinke et al. |
| 9,283,381 B2 | 3/2016 | Grubac et al. |
| 9,283,382 B2 | 3/2016 | Berthiaume et al. |
| 9,289,612 B1 | 3/2016 | Sambelashvili et al. |
| 9,302,115 B2 | 4/2016 | Molin et al. |
| 9,333,364 B2 | 5/2016 | Echt et al. |
| 9,358,387 B2 | 6/2016 | Suwito et al. |
| 9,358,400 B2 | 6/2016 | Jacobson |
| 9,364,675 B2 | 6/2016 | Deterre et al. |
| 9,370,663 B2 | 6/2016 | Moulder |
| 9,375,580 B2 | 6/2016 | Bonner et al. |
| 9,375,581 B2 | 6/2016 | Baru et al. |
| 9,381,365 B2 | 7/2016 | Kibler et al. |
| 9,393,424 B2 | 7/2016 | Demmer et al. |
| 9,393,436 B2 | 7/2016 | Doerr |
| 9,399,139 B2 | 7/2016 | Demmer et al. |
| 9,399,140 B2 | 7/2016 | Cho et al. |
| 9,409,033 B2 | 8/2016 | Jacobson |
| 9,427,594 B1 | 8/2016 | Bornzin et al. |
| 9,433,368 B2 | 9/2016 | Stahmann et al. |
| 9,433,780 B2 | 9/2016 | Régnier et al. |
| 9,457,193 B2 | 10/2016 | Klimovitch et al. |
| 9,492,668 B2 | 11/2016 | Sheldon et al. |
| 9,492,669 B2 | 11/2016 | Demmer et al. |
| 9,492,674 B2 | 11/2016 | Schmidt et al. |
| 9,492,677 B2 | 11/2016 | Greenhut et al. |
| 9,511,233 B2 | 12/2016 | Sambelashvili |
| 9,511,236 B2 | 12/2016 | Varady et al. |
| 9,511,237 B2 | 12/2016 | Deterre et al. |
| 9,522,276 B2 | 12/2016 | Shen et al. |
| 9,522,280 B2 | 12/2016 | Fishler et al. |
| 9,526,522 B2 | 12/2016 | Wood et al. |
| 9,526,891 B2 | 12/2016 | Eggen et al. |
| 9,526,909 B2 | 12/2016 | Stahmann et al. |
| 9,533,163 B2 | 1/2017 | Klimovitch et al. |
| 9,561,382 B2 | 2/2017 | Persson et al. |
| 9,566,012 B2 | 2/2017 | Greenhut et al. |
| 9,636,511 B2 | 5/2017 | Carney et al. |
| 9,669,223 B2 | 6/2017 | Auricchio et al. |
| 9,687,654 B2 | 6/2017 | Sheldon et al. |
| 9,687,655 B2 | 6/2017 | Pertijs et al. |
| 9,687,659 B2 | 6/2017 | Von Arx et al. |
| 9,694,186 B2 | 7/2017 | Carney et al. |
| 9,782,594 B2 | 10/2017 | Stahmann et al. |
| 9,782,601 B2 | 10/2017 | Ludwig |
| 9,789,317 B2 | 10/2017 | Greenhut et al. |
| 9,789,319 B2 | 10/2017 | Sambelashvili |
| 9,808,617 B2 | 11/2017 | Ostroff et al. |
| 9,808,628 B2 | 11/2017 | Sheldon et al. |
| 9,808,631 B2 | 11/2017 | Maile et al. |
| 9,808,632 B2 | 11/2017 | Reinke et al. |
| 9,808,633 B2 | 11/2017 | Bonner et al. |
| 9,808,637 B2 | 11/2017 | Sharma et al. |
| 9,855,414 B2 | 1/2018 | Marshall et al. |
| 9,855,430 B2 | 1/2018 | Ghosh et al. |
| 9,855,435 B2 | 1/2018 | Sahabi et al. |
| 9,861,815 B2 | 1/2018 | Tran et al. |
| 2002/0032470 A1 | 3/2002 | Linberg |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082665 A1 | 6/2002 | Haller et al. |
| 2002/0091414 A1 | 7/2002 | Bardy et al. |
| 2002/0095196 A1 | 7/2002 | Linberg |
| 2002/0099423 A1 | 7/2002 | Berg et al. |
| 2002/0103510 A1 | 8/2002 | Bardy et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0120299 A1 | 8/2002 | Ostroff et al. |
| 2002/0173830 A1 | 11/2002 | Starkweather et al. |
| 2002/0193846 A1 | 12/2002 | Pool et al. |
| 2003/0009203 A1 | 1/2003 | Lebel et al. |
| 2003/0028082 A1 | 2/2003 | Thompson |
| 2003/0040779 A1 | 2/2003 | Engmark et al. |
| 2003/0041866 A1 | 3/2003 | Linberg et al. |
| 2003/0045805 A1 | 3/2003 | Sheldon et al. |
| 2003/0088278 A1 | 5/2003 | Bardy et al. |
| 2003/0097153 A1 | 5/2003 | Bardy et al. |
| 2003/0105497 A1 | 6/2003 | Zhu et al. |
| 2003/0114908 A1 | 6/2003 | Flach |
| 2003/0144701 A1 | 7/2003 | Mehra et al. |
| 2003/0187460 A1 | 10/2003 | Chin et al. |
| 2003/0187461 A1 | 10/2003 | Chin |
| 2004/0024435 A1 | 2/2004 | Leckrone et al. |
| 2004/0068302 A1 | 4/2004 | Rodgers et al. |
| 2004/0087938 A1 | 5/2004 | Leckrone et al. |
| 2004/0088035 A1 | 5/2004 | Guenst et al. |
| 2004/0102830 A1 | 5/2004 | Williams |
| 2004/0127959 A1 | 7/2004 | Amundson et al. |
| 2004/0133242 A1 | 7/2004 | Chapman et al. |
| 2004/0147969 A1 | 7/2004 | Mann et al. |
| 2004/0147973 A1 | 7/2004 | Hauser |
| 2004/0167558 A1 | 8/2004 | Igo et al. |
| 2004/0167587 A1 | 8/2004 | Thompson |
| 2004/0172071 A1 | 9/2004 | Bardy et al. |
| 2004/0172077 A1 | 9/2004 | Chinchoy |
| 2004/0172104 A1 | 9/2004 | Berg et al. |
| 2004/0176817 A1 | 9/2004 | Wahlstrand et al. |
| 2004/0176818 A1 | 9/2004 | Wahlstrand et al. |
| 2004/0176830 A1 | 9/2004 | Fang |
| 2004/0186529 A1 | 9/2004 | Bardy et al. |
| 2004/0204673 A1 | 10/2004 | Flaherty |
| 2004/0210292 A1 | 10/2004 | Bardy et al. |
| 2004/0210293 A1 | 10/2004 | Bardy et al. |
| 2004/0210294 A1 | 10/2004 | Bardy et al. |
| 2004/0215308 A1 | 10/2004 | Bardy et al. |
| 2004/0220624 A1 | 11/2004 | Ritscher et al. |
| 2004/0220626 A1 | 11/2004 | Wagner |
| 2004/0220639 A1 | 11/2004 | Mulligan et al. |
| 2004/0230283 A1 | 11/2004 | Prinzen et al. |
| 2004/0249431 A1 | 12/2004 | Ransbury et al. |
| 2004/0260348 A1 | 12/2004 | Bakken et al. |
| 2004/0267303 A1 | 12/2004 | Guenst |

(56) References Cited

U.S. PATENT DOCUMENTS

| | | |
|---|---|---|
| 2005/0061320 A1 | 3/2005 | Lee et al. |
| 2005/0070962 A1 | 3/2005 | Echt et al. |
| 2005/0102003 A1 | 5/2005 | Grabek et al. |
| 2005/0149138 A1 | 7/2005 | Min et al. |
| 2005/0165466 A1 | 7/2005 | Morris et al. |
| 2005/0182465 A1 | 8/2005 | Ness |
| 2005/0203410 A1 | 9/2005 | Jenkins |
| 2005/0283208 A1 | 12/2005 | Von Arx et al. |
| 2005/0288743 A1 | 12/2005 | Ahn et al. |
| 2006/0042830 A1 | 3/2006 | Maghribi et al. |
| 2006/0052829 A1 | 3/2006 | Sun et al. |
| 2006/0052830 A1 | 3/2006 | Spinelli et al. |
| 2006/0064135 A1 | 3/2006 | Brockway |
| 2006/0064149 A1 | 3/2006 | Belacazar et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095078 A1 | 5/2006 | Tronnes |
| 2006/0106442 A1 | 5/2006 | Richardson et al. |
| 2006/0116746 A1 | 6/2006 | Chin |
| 2006/0135999 A1 | 6/2006 | Bodner et al. |
| 2006/0136004 A1 | 6/2006 | Cowan et al. |
| 2006/0161061 A1 | 7/2006 | Echt et al. |
| 2006/0200002 A1 | 9/2006 | Guenst |
| 2006/0206151 A1 | 9/2006 | Lu |
| 2006/0212079 A1 | 9/2006 | Routh et al. |
| 2006/0241701 A1 | 10/2006 | Markowitz et al. |
| 2006/0241705 A1 | 10/2006 | Neumann et al. |
| 2006/0247672 A1 | 11/2006 | Vidlund et al. |
| 2006/0259088 A1 | 11/2006 | Pastore et al. |
| 2006/0265018 A1 | 11/2006 | Smith et al. |
| 2007/0004979 A1 | 1/2007 | Wojciechowicz et al. |
| 2007/0016098 A1 | 1/2007 | Kim et al. |
| 2007/0027508 A1 | 2/2007 | Cowan |
| 2007/0078490 A1 | 4/2007 | Cowan et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088405 A1 | 4/2007 | Jacobson |
| 2007/0135882 A1 | 6/2007 | Drasler et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0156190 A1 | 7/2007 | Cinbis |
| 2007/0219525 A1 | 9/2007 | Gelfand et al. |
| 2007/0219590 A1 | 9/2007 | Hastings et al. |
| 2007/0225545 A1 | 9/2007 | Ferrari |
| 2007/0233206 A1 | 10/2007 | Frikart et al. |
| 2007/0239244 A1 | 10/2007 | Morgan et al. |
| 2007/0255376 A1 | 11/2007 | Michels et al. |
| 2007/0276444 A1 | 11/2007 | Gelbart et al. |
| 2007/0293900 A1 | 12/2007 | Sheldon et al. |
| 2007/0293904 A1 | 12/2007 | Gelbart et al. |
| 2008/0004663 A1 | 1/2008 | Jorgenson |
| 2008/0021505 A1 | 1/2008 | Hastings et al. |
| 2008/0021519 A1 | 1/2008 | De Geest et al. |
| 2008/0021532 A1 | 1/2008 | Kveen et al. |
| 2008/0065183 A1 | 3/2008 | Whitehurst et al. |
| 2008/0065185 A1 | 3/2008 | Worley |
| 2008/0071318 A1 | 3/2008 | Brooke et al. |
| 2008/0109054 A1 | 5/2008 | Hastings et al. |
| 2008/0119911 A1 | 5/2008 | Rosero |
| 2008/0130670 A1 | 6/2008 | Kim et al. |
| 2008/0154139 A1 | 6/2008 | Shuros et al. |
| 2008/0154322 A1 | 6/2008 | Jackson et al. |
| 2008/0228234 A1 | 9/2008 | Stancer |
| 2008/0234771 A1 | 9/2008 | Chinchoy et al. |
| 2008/0243217 A1 | 10/2008 | Wildon |
| 2008/0269814 A1 | 10/2008 | Rosero |
| 2008/0269825 A1 | 10/2008 | Chinchoy et al. |
| 2008/0275518 A1 | 11/2008 | Ghanem et al. |
| 2008/0275519 A1 | 11/2008 | Ghanem et al. |
| 2008/0288039 A1 | 11/2008 | Reddy |
| 2008/0294208 A1 | 11/2008 | Willis et al. |
| 2008/0294210 A1 | 11/2008 | Rosero |
| 2008/0294229 A1 | 11/2008 | Friedman et al. |
| 2008/0306359 A1 | 12/2008 | Zdeblick et al. |
| 2009/0018599 A1 | 1/2009 | Hastings et al. |
| 2009/0024180 A1 | 1/2009 | Kisker et al. |
| 2009/0036941 A1 | 2/2009 | Corbucci |
| 2009/0048646 A1 | 2/2009 | Katoozi et al. |
| 2009/0062895 A1 | 3/2009 | Stahmann et al. |
| 2009/0082827 A1 | 3/2009 | Kveen et al. |
| 2009/0082828 A1 | 3/2009 | Ostroff |
| 2009/0088813 A1 | 4/2009 | Brockway et al. |
| 2009/0131907 A1 | 5/2009 | Chin et al. |
| 2009/0135886 A1 | 5/2009 | Robertson et al. |
| 2009/0143835 A1 | 6/2009 | Pastore et al. |
| 2009/0171408 A1 | 7/2009 | Solem |
| 2009/0171414 A1 | 7/2009 | Kelly et al. |
| 2009/0204163 A1 | 8/2009 | Shuros et al. |
| 2009/0204170 A1 | 8/2009 | Hastings et al. |
| 2009/0210024 A1 | 8/2009 | M. |
| 2009/0216292 A1 | 8/2009 | Pless et al. |
| 2009/0234407 A1 | 9/2009 | Hastings et al. |
| 2009/0234411 A1 | 9/2009 | Sambelashvili et al. |
| 2009/0266573 A1 | 10/2009 | Engmark et al. |
| 2009/0275998 A1 | 11/2009 | Burnes et al. |
| 2009/0275999 A1 | 11/2009 | Burnes et al. |
| 2009/0299447 A1 | 12/2009 | Jensen et al. |
| 2010/0013668 A1 | 1/2010 | Kantervik |
| 2010/0016911 A1 | 1/2010 | Willis et al. |
| 2010/0023085 A1 | 1/2010 | Wu et al. |
| 2010/0030061 A1 | 2/2010 | Canfield et al. |
| 2010/0030327 A1 | 2/2010 | Chatel |
| 2010/0042108 A1 | 2/2010 | Hibino |
| 2010/0056871 A1 | 3/2010 | Govari et al. |
| 2010/0063375 A1 | 3/2010 | Kassab et al. |
| 2010/0063562 A1 | 3/2010 | Cowan et al. |
| 2010/0069983 A1 | 3/2010 | Peacock, III et al. |
| 2010/0094367 A1 | 4/2010 | Sen |
| 2010/0114209 A1 | 5/2010 | Krause et al. |
| 2010/0114214 A1 | 5/2010 | Morelli et al. |
| 2010/0125281 A1 | 5/2010 | Jacobson et al. |
| 2010/0168761 A1 | 7/2010 | Kassab et al. |
| 2010/0168819 A1 | 7/2010 | Freeberg |
| 2010/0198288 A1 | 8/2010 | Ostroff |
| 2010/0198304 A1 | 8/2010 | Wang |
| 2010/0217367 A1 | 8/2010 | Belson |
| 2010/0228308 A1 | 9/2010 | Cowan et al. |
| 2010/0234906 A1 | 9/2010 | Koh |
| 2010/0234924 A1 | 9/2010 | Willis |
| 2010/0241185 A1 | 9/2010 | Mahapatra et al. |
| 2010/0249729 A1 | 9/2010 | Morris et al. |
| 2010/0286744 A1 | 11/2010 | Echt et al. |
| 2010/0298841 A1 | 11/2010 | Prinzen et al. |
| 2010/0312309 A1 | 12/2010 | Harding |
| 2011/0022113 A1 | 1/2011 | Zdeblick et al. |
| 2011/0071586 A1 | 3/2011 | Jacobson |
| 2011/0077708 A1 | 3/2011 | Ostroff |
| 2011/0112600 A1 | 5/2011 | Cowan et al. |
| 2011/0118588 A1 | 5/2011 | Komblau et al. |
| 2011/0118810 A1 | 5/2011 | Cowan et al. |
| 2011/0137187 A1 | 6/2011 | Yang et al. |
| 2011/0144720 A1 | 6/2011 | Cowan et al. |
| 2011/0152970 A1 | 6/2011 | Jollota et al. |
| 2011/0160558 A1 | 6/2011 | Rassatt et al. |
| 2011/0160565 A1 | 6/2011 | Stubbs et al. |
| 2011/0160801 A1 | 6/2011 | Markowitz et al. |
| 2011/0160806 A1 | 6/2011 | Lyden et al. |
| 2011/0166620 A1 | 7/2011 | Cowan et al. |
| 2011/0166621 A1 | 7/2011 | Cowan et al. |
| 2011/0184491 A1 | 7/2011 | Kivi |
| 2011/0190835 A1 | 8/2011 | Brockway et al. |
| 2011/0208260 A1 | 8/2011 | Jacobson |
| 2011/0218587 A1 | 9/2011 | Jacobson |
| 2011/0230734 A1 | 9/2011 | Fain et al. |
| 2011/0237967 A1 | 9/2011 | Moore et al. |
| 2011/0245890 A1 | 10/2011 | Brisben et al. |
| 2011/0251660 A1 | 10/2011 | Griswold |
| 2011/0251662 A1 | 10/2011 | Griswold et al. |
| 2011/0270099 A1 | 11/2011 | Ruben et al. |
| 2011/0270339 A1 | 11/2011 | Murray, III et al. |

(56) References Cited

U.S. PATENT DOCUMENTS

| | | |
|---|---|---|
| 2011/0270340 A1 | 11/2011 | Pellegrini et al. |
| 2011/0270341 A1 | 11/2011 | Ruben et al. |
| 2011/0276102 A1 | 11/2011 | Cohen |
| 2011/0282423 A1 | 11/2011 | Jacobson |
| 2012/0004527 A1 | 1/2012 | Thompson et al. |
| 2012/0029323 A1 | 2/2012 | Zhao |
| 2012/0041508 A1 | 2/2012 | Rousso et al. |
| 2012/0059433 A1 | 3/2012 | Cowan et al. |
| 2012/0059436 A1 | 3/2012 | Fontaine et al. |
| 2012/0065500 A1 | 3/2012 | Rogers et al. |
| 2012/0078322 A1 | 3/2012 | Dal Molin et al. |
| 2012/0089198 A1 | 4/2012 | Ostroff |
| 2012/0093245 A1 | 4/2012 | Makdissi et al. |
| 2012/0095521 A1 | 4/2012 | Hintz |
| 2012/0095539 A1 | 4/2012 | Khairkhahan et al. |
| 2012/0101540 A1 | 4/2012 | O'Brien et al. |
| 2012/0101553 A1 | 4/2012 | Reddy |
| 2012/0109148 A1 | 5/2012 | Bonner et al. |
| 2012/0109149 A1 | 5/2012 | Bonner et al. |
| 2012/0109236 A1 | 5/2012 | Jacobson et al. |
| 2012/0109259 A1 | 5/2012 | Bond et al. |
| 2012/0116489 A1 | 5/2012 | Khairkhahan et al. |
| 2012/0150251 A1 | 6/2012 | Giftakis et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0172942 A1 | 7/2012 | Berg |
| 2012/0197350 A1 | 8/2012 | Roberts et al. |
| 2012/0197373 A1 | 8/2012 | Khairkhahan et al. |
| 2012/0215285 A1 | 8/2012 | Tahmasian et al. |
| 2012/0232565 A1 | 9/2012 | Kveen et al. |
| 2012/0245665 A1 | 9/2012 | Friedman et al. |
| 2012/0277600 A1 | 11/2012 | Greenhut |
| 2012/0277606 A1 | 11/2012 | Ellingson et al. |
| 2012/0283795 A1 | 11/2012 | Stancer et al. |
| 2012/0283807 A1 | 11/2012 | Deterre et al. |
| 2012/0289776 A1 | 11/2012 | Keast et al. |
| 2012/0289815 A1 | 11/2012 | Keast et al. |
| 2012/0290021 A1 | 11/2012 | Saurkar et al. |
| 2012/0290025 A1 | 11/2012 | Keimel |
| 2012/0296381 A1 | 11/2012 | Matos |
| 2012/0303082 A1 | 11/2012 | Dong et al. |
| 2012/0316613 A1 | 12/2012 | Keefe et al. |
| 2013/0012151 A1 | 1/2013 | Hankins |
| 2013/0023975 A1 | 1/2013 | Locsin |
| 2013/0035748 A1 | 2/2013 | Bonner et al. |
| 2013/0041422 A1 | 2/2013 | Jacobson |
| 2013/0053908 A1 | 2/2013 | Smith et al. |
| 2013/0053915 A1 | 2/2013 | Holmstrom et al. |
| 2013/0053921 A1 | 2/2013 | Bonner et al. |
| 2013/0060298 A1 | 3/2013 | Splett et al. |
| 2013/0066169 A1 | 3/2013 | Rys et al. |
| 2013/0072770 A1 | 3/2013 | Rao et al. |
| 2013/0079798 A1 | 3/2013 | Tran et al. |
| 2013/0079861 A1 | 3/2013 | Reinert et al. |
| 2013/0085350 A1 | 4/2013 | Schugt et al. |
| 2013/0085403 A1 | 4/2013 | Gunderson et al. |
| 2013/0085550 A1 | 4/2013 | Polefko et al. |
| 2013/0096649 A1 | 4/2013 | Martin et al. |
| 2013/0103047 A1 | 4/2013 | Steingisser et al. |
| 2013/0103109 A1 | 4/2013 | Jacobson |
| 2013/0110008 A1 | 5/2013 | Bourget et al. |
| 2013/0110127 A1 | 5/2013 | Bornzin et al. |
| 2013/0110192 A1 | 5/2013 | Tran et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116740 A1 | 5/2013 | Bornzin et al. |
| 2013/0116741 A1 | 5/2013 | Bornzin et al. |
| 2013/0123872 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0138006 A1 | 5/2013 | Bornzin et al. |
| 2013/0150695 A1 | 6/2013 | Biela et al. |
| 2013/0150911 A1 | 6/2013 | Perschbacher et al. |
| 2013/0150912 A1 | 6/2013 | Perschbacher et al. |
| 2013/0184776 A1 | 7/2013 | Shuros et al. |
| 2013/0192611 A1 | 8/2013 | Taepke, II et al. |
| 2013/0196703 A1 | 8/2013 | Masoud et al. |
| 2013/0197609 A1 | 8/2013 | Moore et al. |
| 2013/0231710 A1 | 9/2013 | Jacobson |
| 2013/0238072 A1 | 9/2013 | Deterre et al. |
| 2013/0238073 A1 | 9/2013 | Makdissi et al. |
| 2013/0253309 A1 | 9/2013 | Allan et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0261497 A1 | 10/2013 | Pertijs et al. |
| 2013/0265144 A1 | 10/2013 | Banna et al. |
| 2013/0268042 A1 | 10/2013 | Hastings et al. |
| 2013/0274828 A1 | 10/2013 | Willis |
| 2013/0274847 A1 | 10/2013 | Ostroff |
| 2013/0282070 A1 | 10/2013 | Cowan et al. |
| 2013/0282073 A1 | 10/2013 | Cowan et al. |
| 2013/0296727 A1 | 11/2013 | Sullivan et al. |
| 2013/0303872 A1 | 11/2013 | Taff et al. |
| 2013/0324825 A1 | 12/2013 | Ostroff et al. |
| 2013/0325081 A1 | 12/2013 | Karst et al. |
| 2013/0345770 A1 | 12/2013 | Dianaty et al. |
| 2014/0012344 A1 | 1/2014 | Hastings et al. |
| 2014/0018876 A1 | 1/2014 | Ostroff |
| 2014/0018877 A1 | 1/2014 | Demmer et al. |
| 2014/0031836 A1 | 1/2014 | Ollivier |
| 2014/0039570 A1 | 2/2014 | Carroll et al. |
| 2014/0039591 A1 | 2/2014 | Drasler et al. |
| 2014/0043146 A1 | 2/2014 | Makdissi et al. |
| 2014/0046395 A1 | 2/2014 | Regnier et al. |
| 2014/0046420 A1 | 2/2014 | Moore et al. |
| 2014/0058240 A1 | 2/2014 | Mothilal et al. |
| 2014/0058494 A1 | 2/2014 | Ostroff et al. |
| 2014/0074114 A1 | 3/2014 | Khairkhahan et al. |
| 2014/0074186 A1 | 3/2014 | Faltys et al. |
| 2014/0094891 A1 | 4/2014 | Pare et al. |
| 2014/0100624 A1 | 4/2014 | Ellingson |
| 2014/0100627 A1 | 4/2014 | Min |
| 2014/0107723 A1 | 4/2014 | Hou et al. |
| 2014/0121719 A1 | 5/2014 | Bonner et al. |
| 2014/0121720 A1 | 5/2014 | Bonner et al. |
| 2014/0121722 A1 | 5/2014 | Sheldon et al. |
| 2014/0128935 A1 | 5/2014 | Kumar et al. |
| 2014/0135865 A1 | 5/2014 | Hastings et al. |
| 2014/0142648 A1 | 5/2014 | Smith et al. |
| 2014/0148675 A1 | 5/2014 | Nordstrom et al. |
| 2014/0148815 A1 | 5/2014 | Wenzel et al. |
| 2014/0155950 A1 | 6/2014 | Hastings et al. |
| 2014/0169162 A1 | 6/2014 | Romano et al. |
| 2014/0172060 A1 | 6/2014 | Bornzin et al. |
| 2014/0180306 A1 | 6/2014 | Grubac et al. |
| 2014/0180366 A1 | 6/2014 | Edlund |
| 2014/0207149 A1 | 7/2014 | Hastings et al. |
| 2014/0207210 A1 | 7/2014 | Willis et al. |
| 2014/0214104 A1 | 7/2014 | Greenhut et al. |
| 2014/0222015 A1 | 8/2014 | Keast et al. |
| 2014/0222098 A1 | 8/2014 | Baru et al. |
| 2014/0222109 A1 | 8/2014 | Moulder |
| 2014/0228913 A1 | 8/2014 | Molin et al. |
| 2014/0236172 A1 | 8/2014 | Hastings et al. |
| 2014/0243848 A1 | 8/2014 | Auricchio et al. |
| 2014/0255298 A1 | 9/2014 | Cole et al. |
| 2014/0257324 A1 | 9/2014 | Fain |
| 2014/0257422 A1 | 9/2014 | Herken |
| 2014/0257444 A1 | 9/2014 | Cole et al. |
| 2014/0276929 A1 | 9/2014 | Foster et al. |
| 2014/0303704 A1 | 10/2014 | Suwito et al. |
| 2014/0309706 A1 | 10/2014 | Jacobson |
| 2014/0343348 A1 | 11/2014 | Kaplan et al. |
| 2014/0371818 A1 | 12/2014 | Bond et al. |
| 2014/0379041 A1 | 12/2014 | Foster |

(56) References Cited

U.S. PATENT DOCUMENTS

| | | |
|---|---|---|
| 2015/0025612 A1 | 1/2015 | Haasl et al. |
| 2015/0039041 A1 | 2/2015 | Smith et al. |
| 2015/0045868 A1 | 2/2015 | Bonner et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0057520 A1 | 2/2015 | Foster et al. |
| 2015/0057558 A1 | 2/2015 | Stahmann et al. |
| 2015/0057721 A1 | 2/2015 | Stahmann et al. |
| 2015/0088155 A1 | 3/2015 | Stahmann et al. |
| 2015/0105836 A1 | 4/2015 | Bonner et al. |
| 2015/0126854 A1 | 5/2015 | Keast et al. |
| 2015/0157861 A1 | 6/2015 | Aghassian |
| 2015/0157866 A1 | 6/2015 | Demmer et al. |
| 2015/0173655 A1 | 6/2015 | Demmer et al. |
| 2015/0190638 A1 | 7/2015 | Smith et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |
| 2015/0217119 A1 | 8/2015 | Nikolski et al. |
| 2015/0221898 A1 | 8/2015 | Chi et al. |
| 2015/0224315 A1 | 8/2015 | Stahmann |
| 2015/0224320 A1 | 8/2015 | Stahmann |
| 2015/0230699 A1 | 8/2015 | Berul et al. |
| 2015/0238769 A1 | 8/2015 | Demmer et al. |
| 2015/0258345 A1 | 9/2015 | Smith et al. |
| 2015/0290468 A1 | 10/2015 | Zhang |
| 2015/0297905 A1 | 10/2015 | Greenhut et al. |
| 2015/0297907 A1 | 10/2015 | Zhang |
| 2015/0305637 A1 | 10/2015 | Greenhut et al. |
| 2015/0305638 A1 | 10/2015 | Zhang |
| 2015/0305639 A1 | 10/2015 | Greenhut et al. |
| 2015/0305640 A1 | 10/2015 | Reinke et al. |
| 2015/0305641 A1 | 10/2015 | Stadler et al. |
| 2015/0305642 A1 | 10/2015 | Reinke et al. |
| 2015/0306374 A1 | 10/2015 | Seifert et al. |
| 2015/0306375 A1 | 10/2015 | Marshall et al. |
| 2015/0306401 A1 | 10/2015 | Demmer et al. |
| 2015/0306406 A1 | 10/2015 | Crutchfield et al. |
| 2015/0306407 A1 | 10/2015 | Crutchfield et al. |
| 2015/0306408 A1 | 10/2015 | Greenhut et al. |
| 2015/0321016 A1 | 11/2015 | O'Brien et al. |
| 2015/0328459 A1 | 11/2015 | Chin et al. |
| 2015/0335884 A1 | 11/2015 | Khairkhahan et al. |
| 2016/0015322 A1 | 1/2016 | Anderson et al. |
| 2016/0023000 A1 | 1/2016 | Cho et al. |
| 2016/0030757 A1 | 2/2016 | Jacobson |
| 2016/0033177 A1 | 2/2016 | Barot et al. |
| 2016/0067487 A1 | 3/2016 | Demmer et al. |
| 2016/0121127 A1 | 5/2016 | Klimovitch et al. |
| 2016/0121128 A1 | 5/2016 | Fishler et al. |
| 2016/0121129 A1 | 5/2016 | Persson et al. |
| 2016/0213919 A1 | 7/2016 | Suwito et al. |
| 2016/0213937 A1 | 7/2016 | Reinke et al. |
| 2016/0213939 A1 | 7/2016 | Carney et al. |
| 2016/0228026 A1 | 8/2016 | Jackson |
| 2016/0317825 A1 | 11/2016 | Jacobson |
| 2016/0367823 A1 | 12/2016 | Cowan et al. |
| 2017/0014629 A1 | 1/2017 | Ghosh et al. |
| 2017/0035315 A1 | 2/2017 | Jackson |
| 2017/0043173 A1 | 2/2017 | Sharma et al. |
| 2017/0043174 A1 | 2/2017 | Greenhut et al. |
| 2017/0189681 A1 | 7/2017 | Anderson |
| 2017/0281261 A1 | 10/2017 | Shuros et al. |
| 2017/0281952 A1 | 10/2017 | Shuros et al. |
| 2017/0281953 A1 | 10/2017 | Min et al. |
| 2017/0281955 A1 | 10/2017 | Maile et al. |
| 2017/0312531 A1 | 11/2017 | Sawchuk |

FOREIGN PATENT DOCUMENTS

| | | |
|---|---|---|
| AU | 2014203793 A1 | 7/2014 |
| CA | 1003904 A1 | 1/1977 |
| CN | 202933393 U | 5/2013 |
| EP | 0362611 A1 | 4/1990 |
| EP | 503823 A2 | 9/1992 |
| EP | 1702648 A2 | 9/2006 |
| EP | 1904166 B1 | 6/2011 |
| EP | 2471452 A1 | 7/2012 |
| EP | 2433675 B1 | 1/2013 |
| EP | 2441491 B1 | 1/2013 |
| EP | 2452721 B1 | 11/2013 |
| EP | 2662113 A3 | 11/2013 |
| EP | 1948296 B1 | 1/2014 |
| EP | 2760541 B1 | 5/2016 |
| EP | 2833966 B1 | 5/2016 |
| JP | 2000051373 A | 2/2000 |
| JP | 2002502640 A | 1/2002 |
| JP | 2004512105 A | 4/2004 |
| JP | 2005508208 A | 3/2005 |
| JP | 2005245215 A | 9/2005 |
| JP | 2008540040 A | 11/2008 |
| JP | 5199867 B2 | 2/2013 |
| WO | 9500202 A1 | 1/1995 |
| WO | 9636134 A1 | 11/1996 |
| WO | 9724981 A2 | 7/1997 |
| WO | 9826840 A1 | 6/1998 |
| WO | 9939767 A1 | 8/1999 |
| WO | 0222206 A1 | 3/2002 |
| WO | 0234330 A2 | 5/2002 |
| WO | 02098282 A2 | 12/2002 |
| WO | 2005000206 A3 | 1/2005 |
| WO | 2005042089 A1 | 5/2005 |
| WO | 2006065394 A1 | 6/2006 |
| WO | 2006086435 A3 | 8/2006 |
| WO | 2006113659 A1 | 10/2006 |
| WO | 2006124833 A3 | 11/2006 |
| WO | 2007073435 A1 | 6/2007 |
| WO | 2007075974 A2 | 7/2007 |
| WO | 2009006531 A1 | 1/2009 |
| WO | 2012054102 A1 | 4/2012 |
| WO | 2013080038 A2 | 6/2013 |
| WO | 2013098644 A3 | 7/2013 |
| WO | 2013184787 A1 | 12/2013 |
| WO | 2014120769 A1 | 8/2014 |

OTHER PUBLICATIONS

International Search Report and Written Opinion for Application No. PCT/US2017/047378, 10 pages, dated Dec. 6, 2017.
"Instructions for Use System 1, Leadless Cardiac Pacemaker (LCP) and Delivery Catheter," Nanostim Leadless Pacemakers, pp. 1-28, 2013.
Hachisuka et al., "Development and Performance Analysis of an Intra-Body Communication Device," The 12th International Conference on Solid State Sensors, Actuators and Microsystems, vol. 4A1.3, pp. 1722-1725, 2003.
Seyedi et al., "A Survey on Intrabody Communications for Body Area Network Application," IEEE Transactions on Biomedical Engineering, vol. 60(8): 2067-2079, 2013.
Spickler et al., "Totally Self-Contained Intracardiac Pacemaker," Journal of Electrocardiology, vol. 3(384): 324-331, 1970.
Wegmüller, "Intra-Body Communication for Biomedical Sensor Networks," Diss. ETH, No. 17323, 1-173, 2007.
Rad et al., "Left Ventricular Septum Pacing by Transvenous Approach Through the Interventricular Septum," Maastricht University Medical Center, 18 pages, May 2015.
Henz et al., "Synchronous Ventricular Pacing Without Crossing the Tricuspid Valve or Entering the Coronary Sinus—Preliminary Results," Mayo Clinic, 7 pages, Jun. 8, 2009.
Asirvatham et al., "Intramyocardial Pacing and Sensing for the Enhancement of Cardiac Stimulation and Sensing Specificity," Mayo Clinic, 7 pages, Feb. 14, 2007.
Hyde et al., "Beneficial Effect on Cardiac Resynchronization From Left Ventricular Endocardial Pacing is Mediated by Early Access to

(56) References Cited

OTHER PUBLICATIONS

High Conduction Velocity Tissue," AHA Journals, 18 pages, Jun. 23, 2015.

TRANS SEPTAL IMPLANTABLE MEDICAL DEVICE

CROSS REFERENCE TO RELATED APPLICATIONS

This application claims the benefit of U.S. Provisional Patent Application Ser. No. 62/377,204 filed on Aug. 19, 2016, the disclosure of which is incorporated herein by reference.

TECHNICAL FIELD

The disclosure relates generally to implantable medical devices, and relates more particularly to implantable medical devices that may extend at least partially through a septum within a patient's heart.

BACKGROUND

Implantable medical devices are commonly used today to monitor a patient and/or deliver therapy to a patient. For example, implantable sensors are often used to monitor one or more physiological parameters of a patient, such as heart beats, heart sounds, ECG, respiration, etc. In another example, pacing devices are often used to treat patients suffering from various heart conditions that may result in a reduced ability of the heart to deliver sufficient amounts of blood to a patient's body. Such heart conditions may lead to slow, rapid, irregular, and/or inefficient heart contractions. To help alleviate some of these conditions, various medical devices (e.g., pacemakers, defibrillators, etc.) can be implanted in a patient's body. Such devices may monitor and in some cases provide electrical stimulation to the heart to help the heart operate in a more normal, efficient and/or safe manner. Under some circumstances, it can be beneficial to sense and/or pace two or more chambers of the heart.

SUMMARY

This disclosure relates generally to implantable medical devices, and relates more particularly to implantable medical devices that extend at least partially through a septum within a patient's heart. In some cases, the implantable medical devices may be configured to be disposed adjacent a septum within a patient's heart. In some cases, the implantable medical devices may be configured to extend at least partially into the septum, and in some cases, entirely through the septum. The septum may be the ventricular septum that divides the left and right ventricles. When so provided, the implantable medical device may be configured to sense and/or pace both ventricles of the heart. In some cases, the implantable medical device may be delivered to the ventricle septum via the more accessible right ventricle of the heart. In some cases, the septum may be the atrial septum the divides the left and right atriums. In some cases, the septum may be the atrial/ventricular septum that extends between the right atrium and the left ventricle. These are just examples.

In one example of the disclosure, an implantable medical device (IMD) is configured for deployment at a ventricular septum of a patient's heart, the ventricular septum of the patient's heart having a right ventricle (RV) facing side and a left ventricle (LV) facing side. The IMD may include a housing that includes a proximal end and a distal end. The IMD is configured to be positioned at least in part in the right ventricle (RV) of the patient's heart with the distal end of the housing proximate the RV facing side of the ventricular septum once the IMD is implanted in the patient's heart. The IMD may include a power source that is disposed within the housing, as well as circuitry that is also disposed within the housing and that is operably coupled to the power source. A first RV electrode may be disposed adjacent the distal end of the housing and may be positioned to be facing the RV facing side of the ventricular septum once the IMD is implanted. The first RV electrode may be operatively coupled with the circuitry in the housing. A second RV electrode may be spaced proximally of the first RV electrode and may be operatively coupled with the circuitry in the housing. An LV electrode may be positioned distally of the first RV electrode and at least partially in the ventricular septum once the IMD is implanted. The LV electrode may be operatively coupled with the circuitry in the housing. The IMD may include an LV electrode position adjustment assembly for adjusting a distance that the LV electrode may be positioned distally of the first RV electrode. The LV electrode position adjustment assembly may include a coupling that is secured relative to the housing and that is configured to mate with a separate adjustment tool that can move the coupling relative to the housing to adjust the distance that the LV electrode is positioned distally of the first RV electrode.

Alternatively or additionally to any of the embodiments above, the LV electrode position adjustment assembly may include a fixation helix extending distally from the housing with the LV electrode positioned on the fixation helix. The fixation helix may include a proximal shaft portion extending through a lumen of the housing and terminating in the coupling such that rotating the coupling rotates the fixation helix relative to the housing and causes the fixation helix to thread itself into the ventricular septum.

Alternatively or additionally to any of the embodiments above, the LV electrode position adjustment assembly may include an inner shaft operatively coupled to the coupling and an outer shaft threadedly engaged with the inner shaft and configured to not rotate relative to the housing, wherein rotation of the inner shaft via the coupling results in translation of the outer shaft relative to the housing. The LV electrode may be secured relative to the outer shaft and may translate with the outer shaft.

Alternatively or additionally to any of the embodiments above, at least a portion of the outer shaft has a cross-sectional profile that engages a complementary engagement portion of the housing to prevent rotation of the outer shaft relative to the housing.

Alternatively or additionally to any of the embodiments above, the cross-sectional profile may include a non-circular cross-sectional profile and the complementary engagement portion of the housing may include a distal opening in a lumen that receives at least part of the outer shaft.

Alternatively or additionally to any of the embodiments above, the coupling may include a rotatable tether loop coupled to a proximal end of the inner shaft, such that rotating the rotatable tether loop rotates the inner shaft relative to the outer shaft, thereby causing the outer shaft to translate in response.

Alternatively or additionally to any of the embodiments above, the IMD may further include a spring contact disposed within the housing and operably coupled with the circuitry, the spring contact making sliding electrical contact with a portion of the outer shaft that is electrically coupled with the LV electrode.

Alternatively or additionally to any of the embodiments above, the IMD may further include one or more fixation tines that are configured to extend into the ventricular septum and curve over to anchor the IMD in place relative to the ventricular septum.

Alternatively or additionally to any of the embodiments above, the power source may include a battery.

Alternatively or additionally to any of the embodiments above, the IMD may be a dual chamber leadless cardiac pacemaker (LCP).

In another example of the disclosure, an implantable medical device (IMD) may be configured for deployment within a heart chamber of a patient's heart, near a septum of the patient's heart. The septum of the patient's heart may have a first chamber facing side facing the heart chamber and a second opposing chamber facing side. The IMD may include a housing that is configured to be positioned at least in part in the heart chamber proximate the first chamber facing side of the septum once the IMD is implanted in the patient's heart. The IMD may also include a power source disposed within the housing. Circuitry may be disposed within the housing and may be operatively coupled to the power source. One or more first chamber electrodes that are operatively coupled with the circuitry in the housing may be fixed relative to the housing and may be positioned to be proximate the first chamber facing side of the heart chamber once the IMD is implanted. The housing may define a lumen, and the IMD may include an outer shaft that extends through the lumen and is translatable relative to the lumen. A second chamber electrode may be disposed at or near a distal end of the outer shaft and may be operably coupled with the circuitry disposed within the housing. An inner shaft may be threadedly engaged with the outer shaft such that the inner shaft may be rotated relative to the outer shaft in order to effect translation of the outer shaft relative to the housing. The outer shaft may be translatable between a retracted position in which the second chamber electrode is proximate the first chamber facing side of the septum and an extended position in which the second chamber electrode extends at least partially into the septum.

Alternatively or additionally to any of the embodiments above, at least a portion of the outer shaft may have a cross-sectional profile that engages a complementary engagement portion of the housing to prevent rotation of the outer shaft relative to the housing.

Alternatively or additionally to any of the embodiments above, the inner shaft may extend proximally through the lumen and may terminate in a coupling such that rotating the coupling rotates the inner shaft relative to the outer shaft.

Alternatively or additionally to any of the embodiments above, the IMD may further include one or more fixation tines that are configured to extend into the septum and curve over to anchor the IMD in place relative to the septum.

Alternatively or additionally to any of the embodiments above, the IMD may further include a spring contact disposed within the housing and operably coupled with the circuitry, the spring contact making sliding electrical contact with a portion of the outer shaft that is electrically coupled with the second chamber electrode.

Alternatively or additionally to any of the embodiments above, the LV electrode may serve as an antenna for communication purposes.

Alternatively or additionally to any of the embodiments above, the IMD may be a dual chamber leadless cardiac pacemaker (LCP) and the LCP may sense electrical activity on one side of the ventricular septum and deliver an actionable response on the other side of the ventricular septum.

In another example of the disclosure, a method of facilitating dual chamber pacing of a heart may include advancing an implantable medical device (IMD) to a position proximate a first side of a septum of the heart, the IMD including a housing and two first chamber electrodes disposed relative to the housing, the IMD further including a second chamber electrode and an electrode position adjustment assembly with a coupling for adjusting a position of the second chamber electrode relative to the housing. An adjustment tool may be mated to the coupling of the electrode position adjustment assembly and the adjustment tool may be manipulated to move the coupling relative to the housing to adjust the position of the second chamber electrode relative to the housing. A fixation mechanism may be deployed to secure the IMD relative to the septum.

Alternatively or additionally to any of the embodiments above, the method may further include testing for capture of the heart prior to deploying the fixation mechanism, moving the IMD to a different position proximate the first side of the septum if capture is not achieved, and testing for capture again.

Alternatively or additionally to any of the embodiments above, the method may further include testing for capture with the second chamber electrode positioned at a first distance relative to the housing, manipulating the adjustment tool to move the coupling relative to the housing to adjust the distance that the second chamber electrode is positioned a second distance relative to the housing, and testing for capture again.

The above summary is not intended to describe each and every disclosed embodiment or every implementation of the present disclosure. The Figures and Description which follow more particularly exemplify these and other illustrative embodiments.

BRIEF DESCRIPTION OF THE FIGURES

The disclosure may be more completely understood in consideration of the following description in connection with the accompanying drawings, in which.

Figure 1:
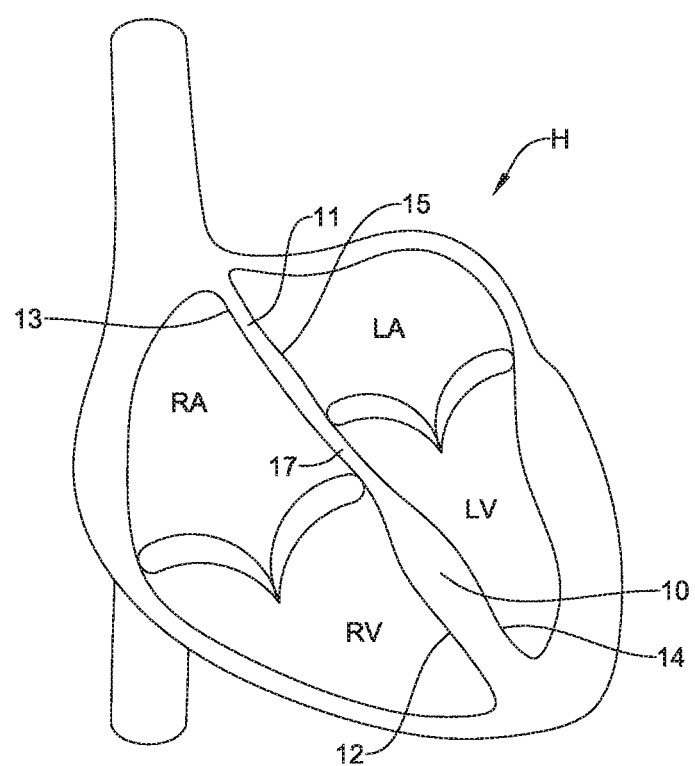
FIG. 1 is a schematic illustration of a human heart.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following description should be read with reference to the drawings in which similar structures in different drawings are numbered the same. The drawings, which are not necessarily to scale, depict illustrative embodiments and are not intended to limit the scope of the disclosure.

FIG. 1 is a schematic illustration of a human heart H. The heart H includes a right side and a left side, relative to the person's perspective. The right side of the heart H includes an RA (right atrium) and an RV (right ventricle). The left side of the heart H includes an LA (left atrium) and an LV (left ventricle). A ventricular septum 10 separates the RV and the LV and an atrial septum 11 separates RA and the LA. The heart H may also be considered as including an atrioventricular septum 17 between the RA and the LV. The ventricular septum 10 may be considered as having an RV facing side 12 and an LV facing side 14. The atrial septum 11 may be considered as including a RA facing side 13 and a RA facing side 15.

It is known that portions of the heart wall, including the ventricular septum 10, have conduction pathways that are involved in causing contractions in the RV and the LV. In some cases, reaching the RV through the vasculature, such as through the superior vena cava or the inferior vena cava and through the right atrium (not illustrated), may be easier than reaching the LV in an intravascular approach. In some cases, debris may be formed within the heart H as a result of placing and manipulating implantable devices within the heart H. In some cases, debris within the RV may be less problematic for the patient than debris within the LV, as debris within the RV may pass into the patient's lungs which can act as a filter while potential debris within the LV may pass directly into the patient's brain, potentially causing a stroke or other complications. Moreover, in some cases, the presence of a significant foreign object (e.g. an implantable medical device) within the heart H may cause tissue ingrowth and/or clotting to occur as a result of the body's natural response to the presence of the foreign body. Such clots, if released, are less of a concern in the RV than the LV.

In some instances, an Implantable Medical Device (IMD) may be configured to be deployed within the RV, next to or proximate the RV facing side 12 of the ventricular septum 10. In some cases, as will be discussed, an IMD may additionally or alternatively be deployed within the RA, next to or proximate the RA facing side 13 of the atrial septum 11. In some cases, a portion of the IMD may, for example, extend partially into the ventricular septum 10, or even completely through the ventricular septum 10, in order to place one or more electrodes in position to capture the aforementioned conduction pathways through the ventricular septum 10 that control the contraction of the LV, or to otherwise sense or pace within the LV. It will be appreciated that in some cases, the portion or portions of the IMD that penetrate into the LV may be minimized in size in order to minimize the body's natural response to such a foreign body. In some cases, the portion or portions of the IMD that penetrate into the LV, and in some instances even the portion or portions of the IMD that remain within the RV, may be coated with or otherwise include one or more anticoagulant materials or materials that encourage endothelialization of the surfaces exposed to blood flow in the chamber.

Figure 2:
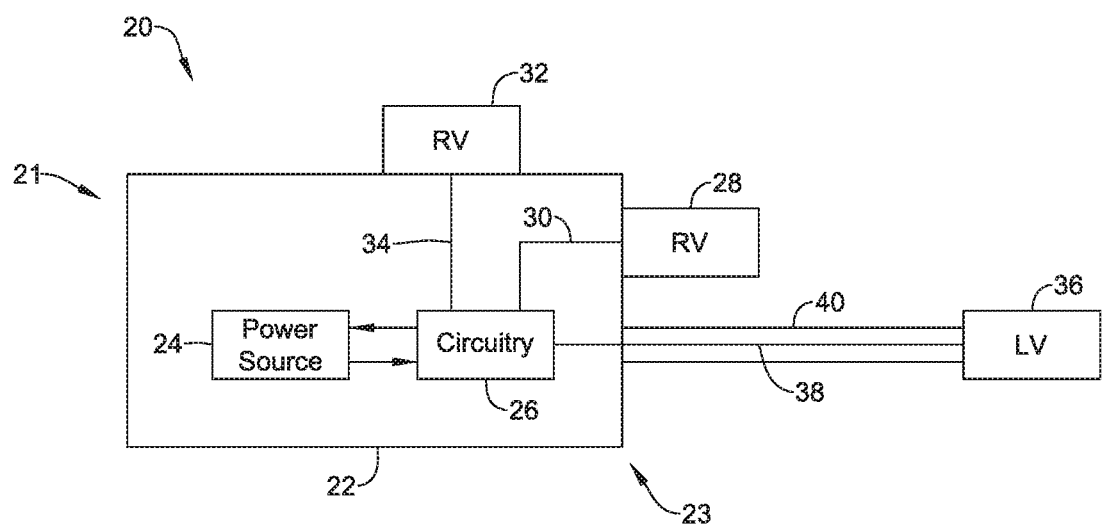
FIG. 2 is a schematic block diagram of an implantable medical device (IMD) in accordance with the disclosure.

FIG. 2 is a highly schematic diagram of an illustrative IMD 20 that may, for example, be utilized proximate the RV facing side 12 of the ventricular septum 10. In some cases, it is envisioned that the IMD 20 may be utilized proximate the RA facing side 13 of the atrial septum 11. In some cases, the septum may be the atrial/ventricular septum 17 that is between the right atrium RA and the left ventricle LV.

In some cases, the IMD 20 may include a housing 22 that may be considered as including a proximal end 21 and a distal end 23. The housing 22 may, for example, be configured to be disposed at least partially within the RV, with the distal end 23 of the housing 22 being next to or proximate the RV facing side 12 of the ventricular septum 10, for example.

A power source 24 may be disposed within the housing 22. In some cases, the power source 24 may be a battery. In some instances, the power source 24 may be a rechargeable power source, such as a rechargeable battery, a capacitor such as a super-capacitor and/or any other suitable rechargeable power source or source capable of harvesting power transmitted wirelessly from another device. In some cases, for example, energy may be transmitted to the power source 24 via RF power transfer. Circuitry 26 may be disposed within the housing 22 and may be operatively coupled to the power source 24 such that the power source 24 can power operation of the circuitry 26. In some cases, if the power source 24 is rechargeable, the circuitry 26 may also regulate recharging operations of the power source 24. In some cases, the circuitry 26 may include or be coupled to an antenna, inductive loop and/or other energy receiving element for wirelessly receiving energy to recharge the battery. In some cases, energy may be harvested from bodily movement.

In some cases, as illustrated, the IMD 20 may include a first RV electrode 28 that is adjacent the distal end 23 of the housing 22. It will be appreciated that the first RV electrode 28 is positioned relative to the housing 22 such that the first RV electrode 28 will be facing the RV facing side 12 of the ventricular septum 10 once the IMD 20 has been implanted. The first RV electrode 28 is operably coupled with the circuitry 26 via a conductor 30. A second RV electrode 32 may be spaced proximally of the first RV electrode 28 and may be operatively coupled with the circuitry 26 via a conductor 34.

In some cases, the IMD 20 may include an LV electrode 36 that, as can be seen, may be positioned distally of the first RV electrode 28. In some cases, the LV electrode 36 may be positioned such that the LV electrode 36 penetrates at least partially into the ventricular septum 10 once the IMD 20 is implanted. In some cases, the LV electrode 36 may extend only partially into the ventricular septum 10. In some instances, the LV electrode 36 may extend all the way through the ventricular septum 10 and may in fact be positioned at the LV facing side 14 of the ventricular septum 10. The LV electrode 36 may be operatively coupled with the circuitry 26 via a conductor 38. In some cases, the IMD 20 may include an LV electrode position adjustment assembly 40 that is schematically shown in FIG. 2. The LV electrode position adjustment assembly 40 may, as will be shown with respect to subsequent Figures, be adjustable in length in order to adjust the position of the LV electrode 36 relative to the housing 22 and thus adjust the relative depth to which the LV electrode 36 penetrates within the ventricular septum 10. In some cases, the LV electrode 36 may function as an antenna for communication purposes.

In some cases, the LV electrode position adjustment assembly 40 may include a threaded mechanism that when rotated causes the LV electrode 36 to move outward to penetrate further into the ventricular septum 10. In some cases, the LV electrode position adjustment assembly 40 may include a push rod that when pushed by a pusher device (e.g. delivery mandrel or catheter) causes the LV electrode 36 to move outward to penetrate further into the ventricular septum 10. In some cases, a latching mechanism may be provided to hold the position of the LV electrode 36 in place. In some cases, the LV electrode position adjustment assembly 40 may telescope and thus may assume a shorter profile in the retracted position. In some cases, the LV electrode position adjustment assembly 40 may include a hydraulic mechanism that when activated moves the LV electrode 36 outward to penetrate further into the ventricular septum 10. In some cases, the LV electrode position adjustment assembly 40 may include an electric motor configured to drive the LV electrode 36 outward to penetrate further into the ventricular septum 10. In some cases, the LV electrode position adjustment assembly 40 may include a solenoid to drive the LV electrode 36 outward to penetrate further into the ventricular septum 10. These are just some examples implantations of the LV electrode position adjustment assembly 40. In some cases, the LV electrode position adjustment assembly 40 may be configured to also retract the LV electrode 36 relative to the ventricular septum 10 and toward the housing 22. When so provided, the positioning of the LV electrode 36 in the ventricular septum 10 may be adjustable in both proximal and distal directions. In some cases, for example, the IMD 20 may sense electrical activity in one portion of the heart H and deliver an actionable response, such as but not limited to pacing, to another portion of the heart H. For example, the IMD 20 may sense electrical activity on the RV facing side 12 of the ventricular septum 10, such as via the RV electrode 28, and may pace on the LV facing side 14 of the ventricular septum 10 using the LV electrode 36.

Figure 3:
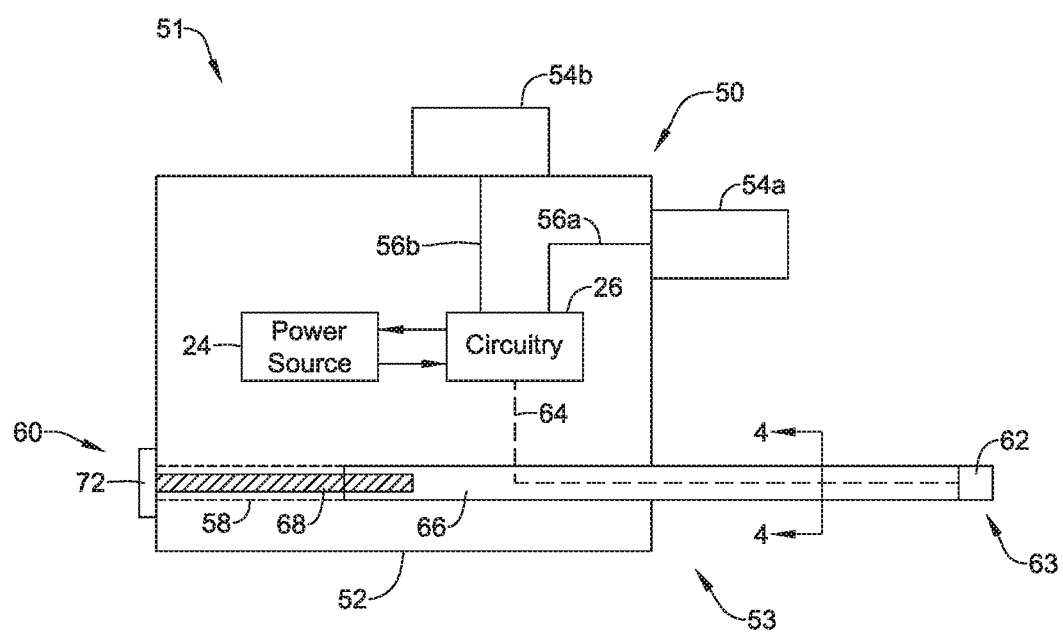
FIG. 3 is a schematic block diagram of an implantable medical device (IMD) in accordance with the disclosure.

FIG. 3 is a highly schematic illustration of an IMD 50 that may be configured for deployment within a heart chamber of a patient's heart, near a septum of the heart. The septum may be considered as having a first chamber facing side that faces the heart chamber and a second opposing chamber facing side. In some cases, the heart chamber may be the RV, and thus the septum in question is the ventricular septum 10, having an RV facing side 12 and an LV facing side 14. This is merely illustrative, as for example the IMD 50 may be implantable within the RA, meaning that the septum in question is the atrial septum 11, having an RA facing side 13 and an LA facing side 15. The IMD 50 includes a housing 52 having a proximal end 51 and a distal end 53.

The IMD 50 may include one or more first chamber electrodes 54 that are fixed relative to the housing 52 and that are positioned to be proximate the first chamber facing side of the heart chamber once the IMD is implanted. As illustrated, the IMD 50 includes a first chamber electrode 54a and a second chamber electrode 54b. The first chamber electrode 54a may be operatively coupled with the circuitry 26 via a conductor 56a. The second chamber electrode 54b may be operatively coupled with the circuitry 26 via a conductor 56b.

In some cases, a lumen 58 may extend through the housing 52 from the proximal end 51 to the distal end 53. As can be seen, an adjustment mechanism 60 may extend through the lumen 58. In some cases, the adjustment mechanism 60 may be considered as being an example of the LV electrode position adjustment assembly 40 referenced in FIG. 2. A second chamber electrode 62 may be seen disposed at or near a distal end 63 of the adjustment mechanism 60 and may be operatively coupled with the circuitry 26 via a conductor 64 (shown partially in phantom). In some cases, the adjustment mechanism 60 may include an outer shaft 66 that extends through the lumen 58, and as will be discussed may be translatable relative to the lumen 58 and housing 52. The adjustment mechanism 60 may include an inner shaft 68 that is threadedly engaged with the outer shaft 66 such that the inner shaft 68 may be rotated relative to the outer shaft 66 in order to effect translation of the outer shaft 66 relative to the housing 52. In some cases, the outer shaft 66 may be translatable between a retracted position in which the second chamber electrode 62 is proximate the first chamber facing side of the septum and an extended position in which the second chamber electrode 62 extends at least partially into the septum. In some cases, a plurality of second chamber electrodes 62 may be provided, each at a different position along the outer shaft 66 so that each is at a different depth in the septum. The circuitry 26 may include a selector (not explicitly shown) to select which one (or more) of the plurality of second chamber electrodes 62 to use.

The outer shaft 66 may be coated with a steroid or other substance to minimize inflammation. In some cases, the outer shaft 66 may have an atraumatic tip at its distal end. The atraumatic tip may be semi-flexible and may be rounded to avoid cutting the myocardium. In some cases, the outer shaft may contain fixation elements, such as flexible talons extending laterally out from the side walls of the outer shaft 66. Such fixation elements may provide additional stability and may be used in in addition to, or in place of, fixation tines 104 (see FIG. 6) and/or anchors 216 (see FIG. 10). In some cases, one or more of the fixation elements may be electrically active, for example.

Figure 4:
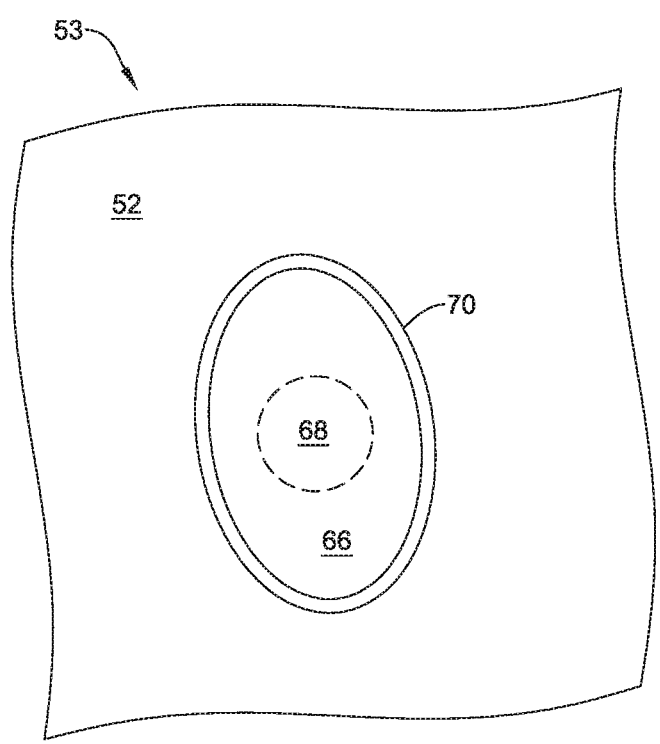
FIG. 4 is an enlarged end view of part of the IMD of FIG. 3.

In some cases, the outer shaft 66 may be constrained against rotating relative to the housing 52. By holding the outer shaft 66 from rotating relative to the housing 52, rotating the inner shaft 68 relative to the outer shaft 66 (and relative to the housing 52) may cause the outer shaft 66 to translate without rotating. In some cases, rotating the inner shaft 68 in a first direction may cause the outer shaft 66 to translate in a distal direction while rotating the inner shaft 68 in a second, opposite direction, may cause the outer shaft 66 to translate in a proximal direction. In some cases, the outer shaft 66 or at least a portion of the outer shaft 66 may have a cross-sectional profile that engages a complementary engagement portion of the housing 52 in order to prevent rotation of the outer shaft 66 relative to the housing 52 while still allowing translation of the outer shaft 66 relative to the housing 52. FIG. 4 provides an enlarged view of part of the distal end 53 of the housing 52 of FIG. 3. The outer shaft 66 is shown as having a cross-sectional profile, such as but not limited to a non-circular cross-sectional profile, which is complementary in shape to an aperture 70 that represents a distal end of the lumen 58. It will be appreciated that this is just one example of a suitable relationship between an outer profile of the outer shaft 66 relative to the aperture 70.

Returning to FIG. 3, the adjustment mechanism 60 may include a coupling 72 that may, for example, be rigidly coupled to the inner shaft 68 such that rotation of the coupling 72 produces rotation of the inner shaft 68. The coupling 72 may be configured such that a separate adjustment tool may be mated with the coupling 72. In some cases, the adjustment tool may be used to rotate the coupling 72 to rotate the inner shaft 68. In some cases, the coupling 72 may, for example, represent a tether loop. Rotating the tether loop may cause the inner shaft 68 to rotate in the same direction as the tether loop, and the rotation of the inner shaft 68 relative to the outer shaft 66 while the outer shaft 66 is constrained from rotating causes translation of the outer shaft 66 relative to the housing 52. It is contemplated that the coupling may be a mechanical coupling, an electrical coupling, a hydraulic coupling and/or any other suitable coupling as desired, depending on the type of LV electrode position adjustment assembly 40 used.

Figure 5:
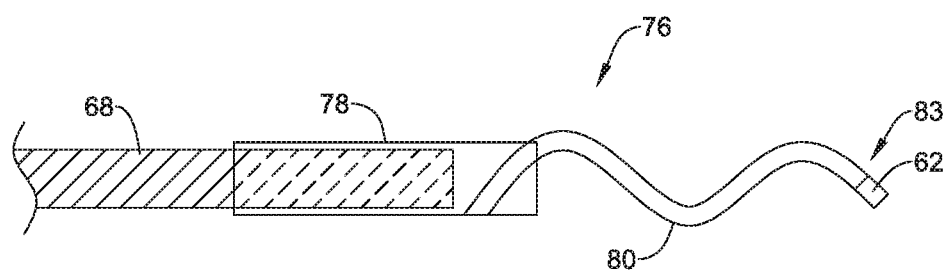
FIG. 5 is a schematic block diagram of another example adjustment mechanism.

Turning to FIG. 5, and in some cases, it is contemplated that the adjustment mechanism 60 may include a fixation helix. FIG. 5 shows an outer shaft 76 that includes a shaft portion 78 and a helix portion 80. In some cases, the shaft portion 78 is threadedly engaged with the inner shaft 68. In some cases, the shaft portion 78 is rigidly coupled with the inner shaft 68 and the shaft portion 78 is not constrained against rotation. In some cases, the inner shaft 68 and the shaft portion 78 may be considered as forming a proximal shaft portion that extends proximally back to the coupling 72 (FIG. 3). As a result, and in some cases, rotation of the inner shaft 68 may cause rotation of the outer shaft 76 such that the helix portion 80 is able to twist or screw itself into the septum. In some cases, the helix portion 80 may be soldered or welded to the inner shaft 68. In some cases, the helix portion 80 may be integrally formed as part of the inner shaft 68. In some cases, the second chamber electrode 62 may be disposed at or near a distal end 83 of the helix portion 80 and may be operatively coupled to circuitry 26. In some cases, a plurality of second chamber electrodes 62 may be provided, each at a different position along the helix portion 80 so that each is at a different depth in the septum. The circuitry 26 may include a selector (not explicitly shown in FIG. 3) to select which one (or more) of the plurality of second chamber electrodes 62 to use.

Figure 6:
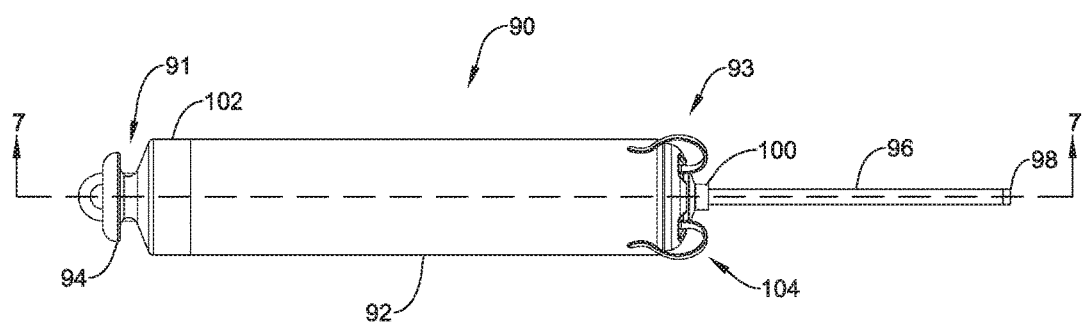
FIG. 6 is a perspective view of an IMD that is a leadless cardiac pacemaker (LCP) in accordance with the disclosure.

FIG. 6 provides an illustration of an IMD 90 that is a leadless cardiac pacemaker (LCP). The IMD 90 includes a housing 92 that extends from a proximal end 91 to a distal end 93. A tether loop 94 is secured relative to the proximal end 91 and may, for example, be considered as being an example of the coupling 72 (FIG. 3). The tether loop 94 may, for example, be used to hold the IMD 90 relative to a delivery device during implantation, and can be engaged with an adjustment tool to rotate the tether loop 94. At the distal end 93, an outer shaft 96 bearing an LV electrode 98 extends distally from the distal end 93. A first RV electrode 100 may be disposed at or near the distal end 93 of the housing 92. In some cases, as shown, a second RV electrode 102 may be disposed at or near the proximal end 91 of the housing 92. In some cases, the second RV electrode 102 may be a ring electrode, but this is not required. The IMD 90 includes fixation tines 104 that may be configured to extend into heart muscle and then curve over on themselves (as illustrated) to anchor the IMD 90 to the heart.

Figure 7:
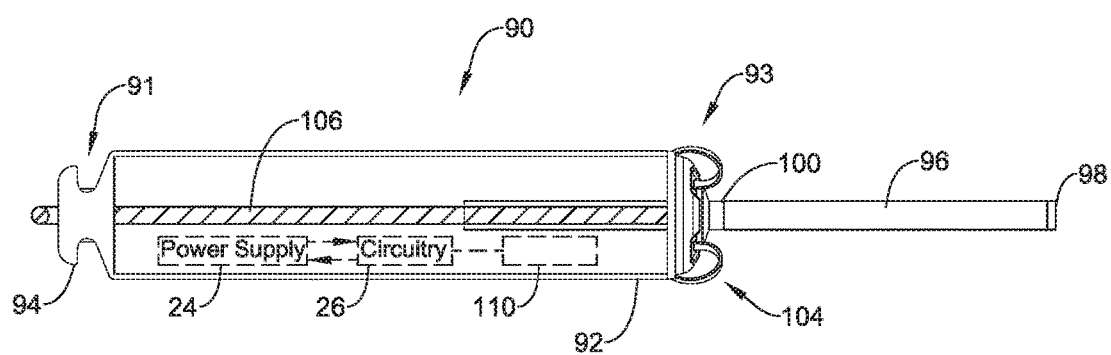
FIG. 7 is a cross-sectional view of the IMD of FIG. 6.

FIG. 7 is a cross-sectional view of the illustrative IMD 90, taken along line 7-7 of FIG. 6. As can be seen, an inner shaft 106 is threadedly engaged with the outer shaft 96 and extends proximally to the tether loop 94 such that rotation of the tether loop 94 causes the inner shaft 106 to rotate relative to the outer shaft 96. If the outer shaft 96 is constrained against rotation relative to the housing 92 (as discussed with respect to FIG. 4, for example), rotation of the tether loop 94 relative to the housing 92 will cause the outer shaft 96 to translate either distally or proximally, depending on the threading direction of the inner shaft 106 and the outer shaft 96, and the direction in which the tether loop 94 is rotated.

Figure 8:
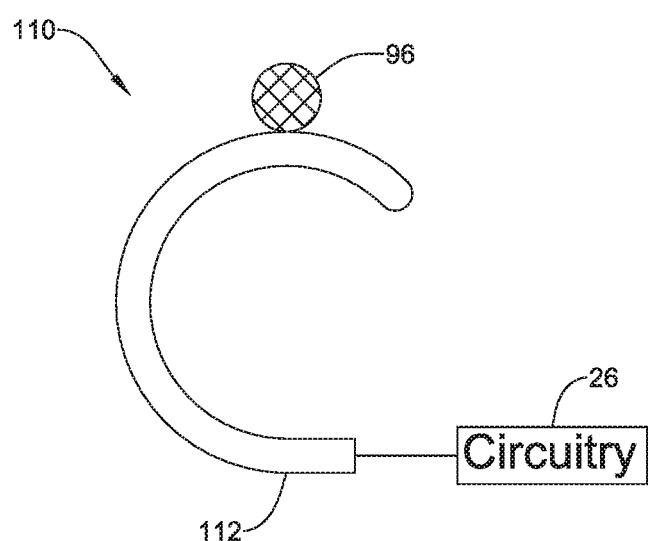
FIG. 8 is a schematic view of a certain components of the IMD of FIG. 6.

It will be appreciated that there needs to be an electrical connection between the circuitry 26 (FIGS. 2, 3 and 7) and the LV electrode 98. As shown schematically in FIG. 7, a connector 110 provides an electrical connection between the circuitry 26 and the moving outer shaft 96. FIG. 8 provides greater detail regarding an illustrative but non-limiting example of the connector 110. In some cases, a spring contact 112 may be coupled with the circuitry 26. The spring contact 112 may make sliding electrical contact with a portion of the outer shaft 96 that is electrically coupled with the LV electrode 98.

Figure 9:
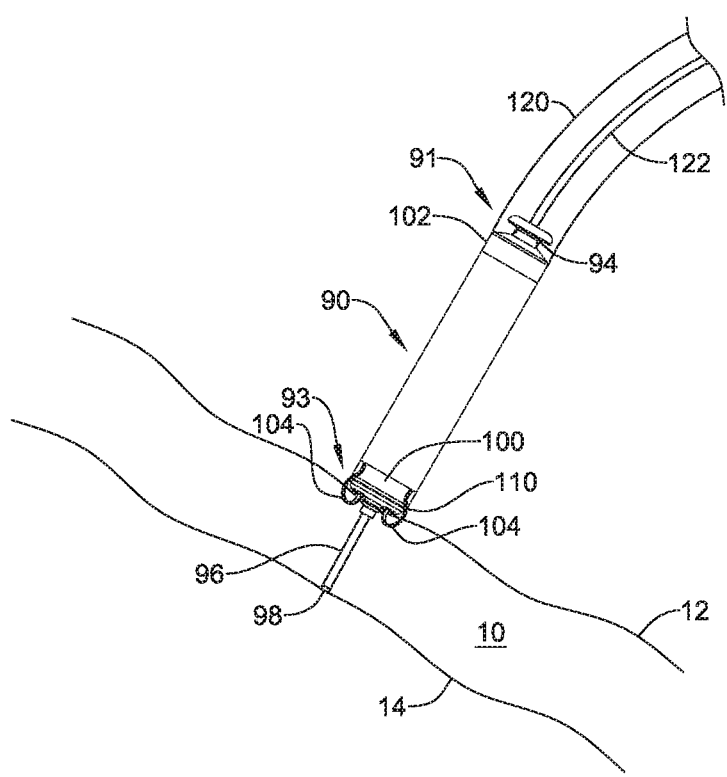
FIG. 9 is a schematic view of an IMD in combination with a delivery device in accordance with the disclosure.

FIG. 9 provides an example of implanting the IMD 90 proximate the ventricular septum 10. As illustrated, the first RV electrode 100 and the second RV electrode 102 are both ring electrodes, but this is not required. The IMD 90 is secured within a delivery device 120, which includes an implantation tool 122 that extends within the delivery device 120 and that may be used for several purposes. For example, the implantation tool 122 may engage the tether loop 94 to hold the IMD 90 relative to the delivery device 120 while delivering the IMD 90 to the implantation site. In some cases, the implantation tool 122 may subsequently be used to rotate the tether loop 94 relative to the housing of the IMD 90 and thus extend or retract the outer shaft 96 bearing the LV electrode 98. As shown, the LV electrode 98 is proximate the LV facing side 14 of the ventricular septum 10. In some cases, the LV electrode 98 may instead be disposed within the ventricular septum 10, at an intermediate depth between the RV facing side 12 of the ventricular septum 10 and the LV facing side 14 of the ventricular septum 10. In some cases, a plurality of LV electrodes may be provided, each at a different position along the outer shaft 96 so that each is at a different depth in the ventricular septum 10. The circuitry 26 may include a selector (not explicitly shown) to select which one (or more) of the plurality of LV electrodes to use.

Figure 10:
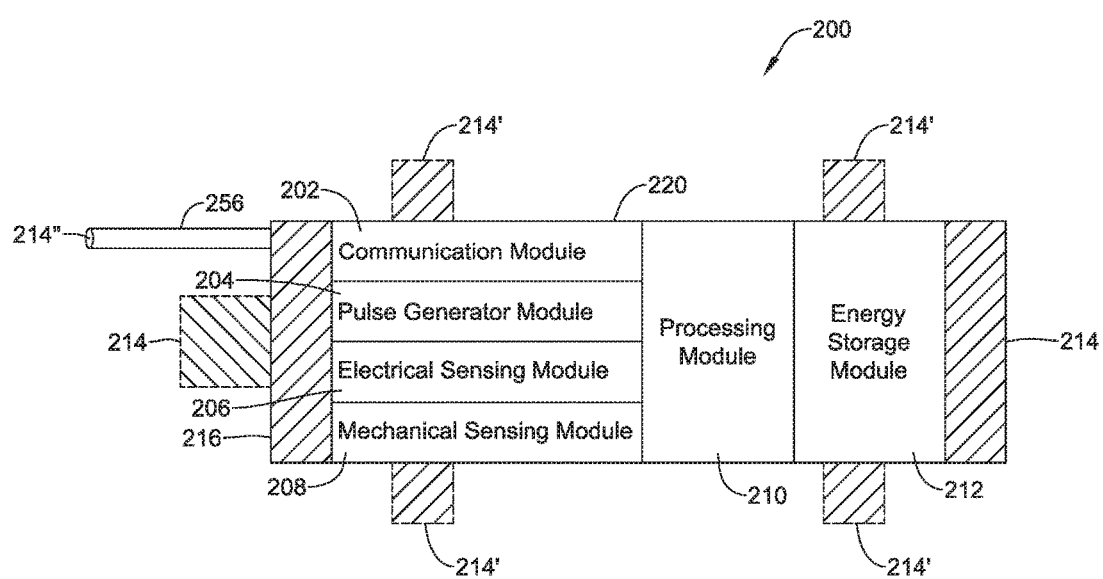
FIG. 10 is a schematic block diagram of an illustrative leadless cardiac pacemaker (LCP), which may be considered as being an example of one of the IMDs of FIGS. 2, 3 and 6.

FIG. 10 is a conceptual schematic block diagram of an illustrative IMD, and more specifically a leadless cardiac pacemaker (LCP) that may operate to sense physiological signals and parameters and deliver one or more types of electrical stimulation therapy to the heart of the patient.

Example electrical stimulation therapy may include bradycardia pacing, rate responsive pacing therapy, cardiac resynchronization therapy (CRT), anti-tachycardia pacing (ATP) therapy and/or the like. As can be seen in FIG. 10, the LCP 200 may be a compact device with all components housed within the LCP 200 or directly on a housing 220. In some instances, the LCP 200 may include one or more of a communication module 202, a pulse generator module 204, an electrical sensing module 206, a mechanical sensing module 208, a processing module 210, an energy storage module 212, and electrodes 214. The LCP 200 may, for example, be considered as being an example of the IMD 20 (FIG. 2), the IMD 50 (FIG. 3) and/or the IMD 90 (FIG. 6).

As depicted in FIG. 10, the LCP 200 may include electrodes 214, which can be secured relative to the housing 220 and electrically exposed to tissue and/or blood surrounding the LCP 200. The electrodes 214 may generally conduct electrical signals to and from the LCP 200 and the surrounding tissue and/or blood. Such electrical signals can include communication signals, electrical stimulation pulses, and intrinsic cardiac electrical signals, to name a few. Intrinsic cardiac electrical signals may include electrical signals generated by the heart and may be represented by an electrocardiogram (ECG).

The electrodes 214 may include one or more biocompatible conductive materials such as various metals or alloys that are known to be safe for implantation within a human body. In some instances, the electrodes 214 may be generally disposed on either end of the LCP 200 and may be in electrical communication with one or more of the modules 202, 204, 206, 208, and 210. In embodiments where the electrodes 214 are secured directly to the housing 220, an insulative material may electrically isolate the electrodes 214 from adjacent electrodes, the housing 220, and/or other parts of the LCP 200. In some instances, some or all of the electrodes 214 may be spaced from the housing 220 and may be connected to the housing 220 and/or other components of the LCP 200 through connecting wires. In such instances, the electrodes 214 may be placed on a tail (not shown) that extends out away from the housing 220. As shown in FIG. 10, in some embodiments, the LCP 200 may include electrodes 214'. The electrodes 214' may be in addition to the electrodes 214, or may replace one or more of the electrodes 214. The electrodes 214' may be similar to the electrodes 214 except that the electrodes 214' are disposed on the sides of the LCP 200. In some cases, the electrodes 214' may increase the number of electrodes by which the LCP 200 may deliver communication signals and/or electrical stimulation pulses, and/or may sense intrinsic cardiac electrical signals, communication signals, and/or electrical stimulation pulses.

The electrodes 214 and/or 114' may assume any of a variety of sizes and/or shapes, and may be spaced at any of a variety of spacings. For example, the electrodes 214 may have an outer diameter of two to twenty millimeters (mm). In other embodiments, the electrodes 214 and/or 114' may have a diameter of two, three, five, seven millimeters (mm), or any other suitable diameter, dimension and/or shape. Example lengths for the electrodes 214 and/or 214' may include, for example, one, three, five, ten millimeters (mm), or any other suitable length. As used herein, the length is a dimension of the electrodes 214 and/or 214' that extends away from the outer surface of the housing 220. In some instances, at least some of the electrodes 214 and/or 214' may be spaced from one another by a distance of twenty, thirty, forty, fifty millimeters (mm), or any other suitable spacing. The electrodes 214 and/or 214' of a single device may have different sizes with respect to each other, and the spacing and/or lengths of the electrodes on the device may or may not be uniform.

In some instances, an LV electrode 214" may also be provided. The LV electrode 214" may be supported by an LV electrode support 256 that extends away from the housing 220. In some cases, the LV electrode support 256 is configured to place the LV electrode 214" within the ventricular septum 10, and in electrical communication with conduction pathways extending through the ventricular septum 10 that control the contraction of the LV. In some instances, the LV electrode support 256 may extend entirely through the ventricular septum 10 in order to place an LV electrode 214" within the LV and in contact with the LV facing side 14 of the ventricular septum 10.

In the embodiment shown, the communication module 202 may be electrically coupled to two or more of the electrodes 214, 214' and/or 214" and may be configured to deliver communication pulses to tissues of the patient for communicating with other devices such as sensors, programmers, other medical devices, and/or the like. Communication signals, as used herein, may be any modulated signal that conveys information to another device, either by itself or in conjunction with one or more other modulated signals. In some embodiments, communication signals may be limited to sub-threshold signals that do not result in capture of the heart yet still convey information. The communication signals may be delivered to another device that is located either external or internal to the patient's body. In some instances, the communication may take the form of distinct communication pulses separated by various amounts of time. In some of these cases, the timing between successive pulses may convey information. The communication module 202 may additionally be configured to sense for communication signals delivered by other devices, which may be located external or internal to the patient's body.

The communication module 202 may communicate to help accomplish one or more desired functions. Some example functions include delivering sensed data, using communicated data for determining occurrences of events such as arrhythmias, coordinating delivery of electrical stimulation therapy, and/or other functions. In some cases, the LCP 200 may use communication signals to communicate raw information, processed information, messages and/or or commands, and/or other data. Raw information may include information such as sensed electrical signals (e.g. a sensed ECG), signals gathered from coupled sensors, and the like. In some embodiments, the processed information may include signals that have been filtered using one or more signal processing techniques. Processed information may also include parameters and/or events that are determined by the LCP 200 and/or another device, such as a determined heart rate, timing of determined heartbeats, timing of other determined events, determinations of threshold crossings, expirations of monitored time periods, accelerometer signals, activity level parameters, blood-oxygen parameters, blood pressure parameters, heart sound parameters, and the like. In some cases, processed information may, for example, be provided by a chemical sensor or an optically interfaced sensor. Messages and/or commands may include instructions or the like directing another device to take action, notifications of imminent actions of the sending device, requests for reading from the receiving device, requests for writing data to the receiving device, information messages, and/or other messages commands.

In at least some embodiments, the communication module 202 (or the LCP 200) may further include switching circuitry to selectively connect one or more of the electrodes 214, 214' and/or 214" to the communication module 202 in order to select which of the electrodes 214, 214' and/or 214" that the communication module 202 delivers communication pulses with. It is contemplated that the communication module 202 may be communicating with other devices via conducted signals, radio frequency (RF) signals, optical signals, acoustic signals, inductive coupling, and/or any other suitable communication methodology. Where the communication module 202 generates electrical communication signals, the communication module 202 may include one or more capacitor elements and/or other charge storage devices to aid in generating and delivering communication signals. In the embodiment shown, the communication module 202 may use energy stored in the energy storage module 212 to generate the communication signals. In at least some examples, the communication module 202 may include a switching circuit that is connected to the energy storage module 212 and, with the switching circuitry, may connect the energy storage module 212 to one or more of the electrodes 214/214'/214" to generate the communication signals.

As shown in FIG. 10, a pulse generator module 204 may be electrically connected to one or more of the electrodes 214, 214' and/or 214". The pulse generator module 204 may be configured to generate electrical stimulation pulses and deliver the electrical stimulation pulses to tissues of a patient via one or more of the electrodes 214, 214' and/or 214" in order to effectuate one or more electrical stimulation therapies. Electrical stimulation pulses as used herein are meant to encompass any electrical signals that may be delivered to tissue of a patient for purposes of treatment of any type of disease or abnormality. For example, when used to treat heart disease, the pulse generator module 204 may generate electrical stimulation pacing pulses for capturing the heart of the patient, i.e. causing the heart to contract in response to the delivered electrical stimulation pulse. In some of these cases, the LCP 200 may vary the rate at which the pulse generator module 204 generates the electrical stimulation pulses, for example in rate adaptive pacing. In other embodiments, the electrical stimulation pulses may include defibrillation/cardioversion pulses for shocking the heart out of fibrillation or into a normal heart rhythm. In yet other embodiments, the electrical stimulation pulses may include anti-tachycardia pacing (ATP) pulses. It should be understood that these are just some examples. The pulse generator module 204 may include one or more capacitor elements and/or other charge storage devices to aid in generating and delivering appropriate electrical stimulation pulses. In at least some embodiments, the pulse generator module 204 may use energy stored in the energy storage module 212 to generate the electrical stimulation pulses. In some particular embodiments, the pulse generator module 204 may include a switching circuit that is connected to the energy storage module 212 and may connect the energy storage module 212 to one or more of the electrodes 214/214'/214" to generate electrical stimulation pulses. In some cases, the pulse generator module 204 may provide pacing pulses to pace the RV of the heart H using electrode 214, and may provide pacing pulses to the LV of the heart H using electrode 214". In some cases, the pacing pulses generated for pacing the RV of the heart H by the pulse generator module 204 may be offset in time, have a different duration, have a different amplitude and/or have a different shape from the pacing pulses generated by the pulse generator module 204 for pacing the LV of the heart H, if desired.

The LCP 200 may further include an electrical sensing module 206 and a mechanical sensing module 208. The electrical sensing module 206 may be configured to sense intrinsic cardiac electrical signals conducted from the electrodes 214, 214' and/or 214" to the electrical sensing module 206. For example, the electrical sensing module 206 may be electrically connected to one or more of the electrodes 214, 214' and/or 214" and the electrical sensing module 206 may be configured to receive cardiac electrical signals conducted through the electrodes 214, 214' and/or 214" via a sensor amplifier or the like. In some embodiments, the cardiac electrical signals from electrodes 214 and/or 214' may represent local information from the RV, while the cardiac electrical signals from LV electrode 214" may represent local information from the LV of the heart H.

The mechanical sensing module 208 may include, or be electrically connected to, various sensors, such as accelerometers, including multi-axis accelerometers such as two- or three-axis accelerometers, gyroscopes, including multi-axis gyroscopes such as two- or three-axis gyroscopes, blood pressure sensors, heart sound sensors, piezoelectric sensors, blood-oxygen sensors, and/or other sensors which measure one or more physiological parameters of the heart and/or patient. Mechanical sensing module 208, when present, may gather signals from the sensors indicative of the various physiological parameters. The electrical sensing module 206 and the mechanical sensing module 208 may both be connected to the processing module 210 and may provide signals representative of the sensed cardiac electrical signals and/or physiological signals to the processing module 210. Although described with respect to FIG. 10 as separate sensing modules, in some embodiments, the electrical sensing module 206 and the mechanical sensing module 208 may be combined into a single module. In at least some examples, the LCP 200 may only include one of the electrical sensing module 206 and the mechanical sensing module 208. In some cases, any combination of the processing module 210, the electrical sensing module 206, the mechanical sensing module 208, the communication module 202, the pulse generator module 204 and/or the energy storage module may be considered a controller of the LCP 200.

The processing module 210 may be configured to direct the operation of the LCP 200 and may, in some embodiments, be termed a controller. For example, the processing module 210 may be configured to receive cardiac electrical signals from the electrical sensing module 206 and/or physiological signals from the mechanical sensing module 208. Based on the received signals, the processing module 210 may determine, for example, occurrences and types of arrhythmias and other determinations such as whether the LCP 200 has become dislodged. The processing module 210 may further receive information from the communication module 202. In some embodiments, the processing module 210 may additionally use such received information to determine occurrences and types of arrhythmias and/or and other determinations such as whether the LCP 200 has become dislodged. In still some additional embodiments, the LCP 200 may use the received information instead of the signals received from the electrical sensing module 206 and/or the mechanical sensing module 208—for instance if the received information is deemed to be more accurate than the signals received from the electrical sensing module 206 and/or the mechanical sensing module 208 or if the electrical sensing module 206 and/or the mechanical sensing module 208 have been disabled or omitted from the LCP 200.

After determining an occurrence of an arrhythmia, the processing module 210 may control the pulse generator module 204 to generate electrical stimulation pulses in accordance with one or more electrical stimulation therapies to treat the determined arrhythmia. For example, the processing module 210 may control the pulse generator module 204 to generate pacing pulses with varying parameters and in different sequences to effectuate one or more electrical stimulation therapies. As one example, in controlling the pulse generator module 204 to deliver bradycardia pacing therapy, the processing module 210 may control the pulse generator module 204 to deliver pacing pulses designed to capture the heart of the patient at a regular interval to help prevent the heart of a patient from falling below a predetermined threshold. In some cases, the rate of pacing may be increased with an increased activity level of the patient (e.g. rate adaptive pacing). For instance, the processing module 210 may monitor one or more physiological parameters of the patient which may indicate a need for an increased heart rate (e.g. due to increased metabolic demand). The processing module 210 may then increase the rate at which the pulse generator module 204 generates electrical stimulation pulses. Adjusting the rate of delivery of the electrical stimulation pulses based on the one or more physiological parameters may extend the battery life of the LCP 200 by only requiring higher rates of delivery of electrical stimulation pulses when the physiological parameters indicate there is a need for increased cardiac output. Additionally, adjusting the rate of delivery of the electrical stimulation pulses may increase a comfort level of the patient by more closely matching the rate of delivery of electrical stimulation pulses with the cardiac output need of the patient.

For ATP therapy, the processing module 210 may control the pulse generator module 204 to deliver pacing pulses at a rate faster than an intrinsic heart rate of a patient in attempt to force the heart to beat in response to the delivered pacing pulses rather than in response to intrinsic cardiac electrical signals. Once the heart is following the pacing pulses, the processing module 210 may control the pulse generator module 204 to reduce the rate of delivered pacing pulses down to a safer level. In CRT, the processing module 210 may control the pulse generator module 204 to deliver pacing pulses in coordination with another device to cause the heart to contract more efficiently. In cases where the pulse generator module 204 is capable of generating defibrillation and/or cardioversion pulses for defibrillation/cardioversion therapy, the processing module 210 may control the pulse generator module 204 to generate such defibrillation and/or cardioversion pulses. In some cases, the processing module 210 may control the pulse generator module 204 to generate electrical stimulation pulses to provide electrical stimulation therapies different than those examples described above.

Aside from controlling the pulse generator module 204 to generate different types of electrical stimulation pulses and in different sequences, in some embodiments, the processing module 210 may also control the pulse generator module 204 to generate the various electrical stimulation pulses with varying pulse parameters. For example, each electrical stimulation pulse may have a pulse width and a pulse amplitude. The processing module 210 may control the pulse generator module 204 to generate the various electrical stimulation pulses with specific pulse widths and pulse amplitudes. For example, the processing module 210 may cause the pulse generator module 204 to adjust the pulse width and/or the pulse amplitude of electrical stimulation pulses if the electrical stimulation pulses are not effectively capturing the heart (e.g. RV or LV capture). Such control of the specific parameters of the various electrical stimulation pulses may help the LCP 200 provide more effective delivery of electrical stimulation therapy.

In some embodiments, the processing module 210 may further control the communication module 202 to send information to other devices. For example, the processing module 210 may control the communication module 202 to generate one or more communication signals for communicating with other devices of a system of devices. For instance, the processing module 210 may control the communication module 202 to generate communication signals in particular pulse sequences, where the specific sequences convey different information. The communication module 202 may also receive communication signals for potential action by the processing module 210.

In further embodiments, the processing module 210 may control switching circuitry by which the communication module 202 and the pulse generator module 204 deliver communication signals and/or electrical stimulation pulses to tissue of the patient. As described above, both the communication module 202 and the pulse generator module 204 may include circuitry for connecting one or more of the electrodes 214, 214' and/or 214" to the communication module 202 and/or the pulse generator module 204 so those modules may deliver the communication signals and electrical stimulation pulses to tissue of the patient. The specific combination of one or more electrodes by which the communication module 202 and/or the pulse generator module 204 deliver communication signals and electrical stimulation pulses may influence the reception of communication signals and/or the effectiveness of electrical stimulation pulses. Although it was described that each of the communication module 202 and the pulse generator module 204 may include switching circuitry, in some embodiments, the LCP 200 may have a single switching module connected to the communication module 202, the pulse generator module 204, and the electrodes 214, 214' and/or 214". In such embodiments, processing module 210 may control the switching module to connect the modules 202/204 and the electrodes 214/214'/214" as appropriate. In some cases, the LV electrode 214" may also be coupled to the switching module and may be used for communication.

In some embodiments, the processing module 210 may include a pre-programmed chip, such as a very-large-scale integration (VLSI) chip or an application specific integrated circuit (ASIC). In such embodiments, the chip may be pre-programmed with control logic in order to control the operation of the LCP 200. By using a pre-programmed chip, the processing module 210 may use less power than other programmable circuits while able to maintain basic functionality, thereby potentially increasing the battery life of the LCP 200. In other instances, the processing module 210 may include a programmable microprocessor or the like. Such a programmable microprocessor may allow a user to adjust the control logic of the LCP 200 after manufacture, thereby allowing for greater flexibility of the LCP 200 than when using a pre-programmed chip. In still other embodiments, the processing module 210 may not be a single component. For example, the processing module 210 may include multiple components positioned at disparate locations within the LCP 200 in order to perform the various described functions. For example, certain functions may be performed in one component of the processing module 210, while other functions are performed in a separate component of the processing module 210.

The processing module 210, in additional embodiments, may include a memory circuit and the processing module 210 may store information on and read information from the memory circuit. In other embodiments, the LCP 200 may include a separate memory circuit (not shown) that is in communication with the processing module 210, such that the processing module 210 may read and write information to and from the separate memory circuit. The memory circuit, whether part of the processing module 210 or separate from the processing module 210, may be volatile memory, non-volatile memory, or a combination of volatile memory and non-volatile memory.

The energy storage module 212 may provide a power source to the LCP 200 for its operations. In some embodiments, the energy storage module 212 may be a non-rechargeable lithium-based battery. In other embodiments, the non-rechargeable battery may be made from other suitable materials. In some embodiments, the energy storage module 212 may be considered to be a rechargeable power supply, such as but not limited to, a rechargeable battery. In still other embodiments, the energy storage module 212 may include other types of energy storage devices such as capacitors or super capacitors. In some cases, as will be discussed, the energy storage module 212 may include a rechargeable primary battery and a non-rechargeable secondary battery. In some cases, the primary battery and the second battery, if present, may both be rechargeable.

To implant the LCP 200 inside a patient's body, an operator (e.g., a physician, clinician, etc.), may fix the LCP 200 to the cardiac tissue of the patient's heart. To facilitate fixation, the LCP 200 may include one or more anchors 216. The one or more anchors 216 may include any number of fixation or anchoring mechanisms. For example, one or more anchors 216 may include one or more pins, staples, threads, screws, helix, tines, and/or the like. In some embodiments, although not shown, one or more anchors 216 may include threads on its external surface that may run along at least a partial length of an anchor member. The threads may provide friction between the cardiac tissue and the anchor to help fix the anchor member within the cardiac tissue. In some cases, the one or more anchors 216 may include an anchor member that has a cork-screw shape that can be screwed into the cardiac tissue. In other embodiments, the anchor 216 may include other structures such as barbs, spikes, or the like to facilitate engagement with the surrounding cardiac tissue.

Figure 11:
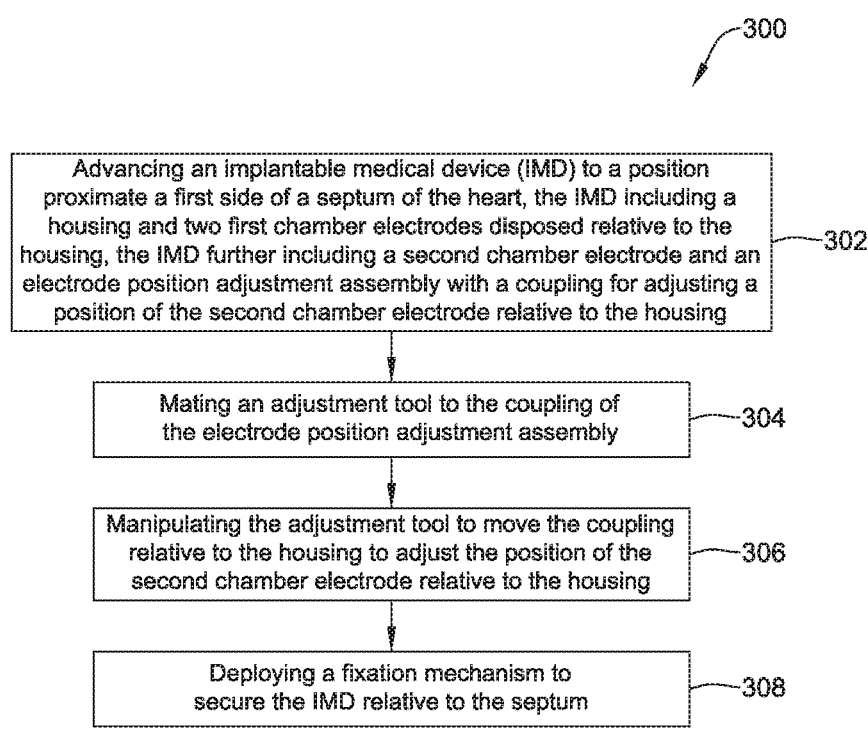
FIG. 11 is a flow diagram showing an illustrative method of facilitating dual chamber cardiac pacing.

FIG. 11 is a flow diagram showing an illustrative method 300 for facilitating dual chamber cardiac pacing. In some cases, and as shown at block 302, the method 300 includes advancing an IMD (such as but not limited to the IMD 20, the IMD 50 and/or the IMD 90) to a position proximate a first side of a septum of the heart, the IMD including a housing and two first chamber electrodes disposed relative to the housing, the IMD further including a second chamber electrode and an electrode position adjustment assembly with a coupling for adjusting a position of the second chamber electrode relative to the housing. As seen at block 304, an adjustment tool may be mated to the coupling of the electrode position adjustment assembly. The adjustment tool may be manipulated to move the coupling relative to the housing to adjust the position of the second chamber electrode relative to the housing as seen at block 306. As indicated at block 308, a fixation mechanism may be deployed to secure the IMD relative to the septum.

Figure 12:
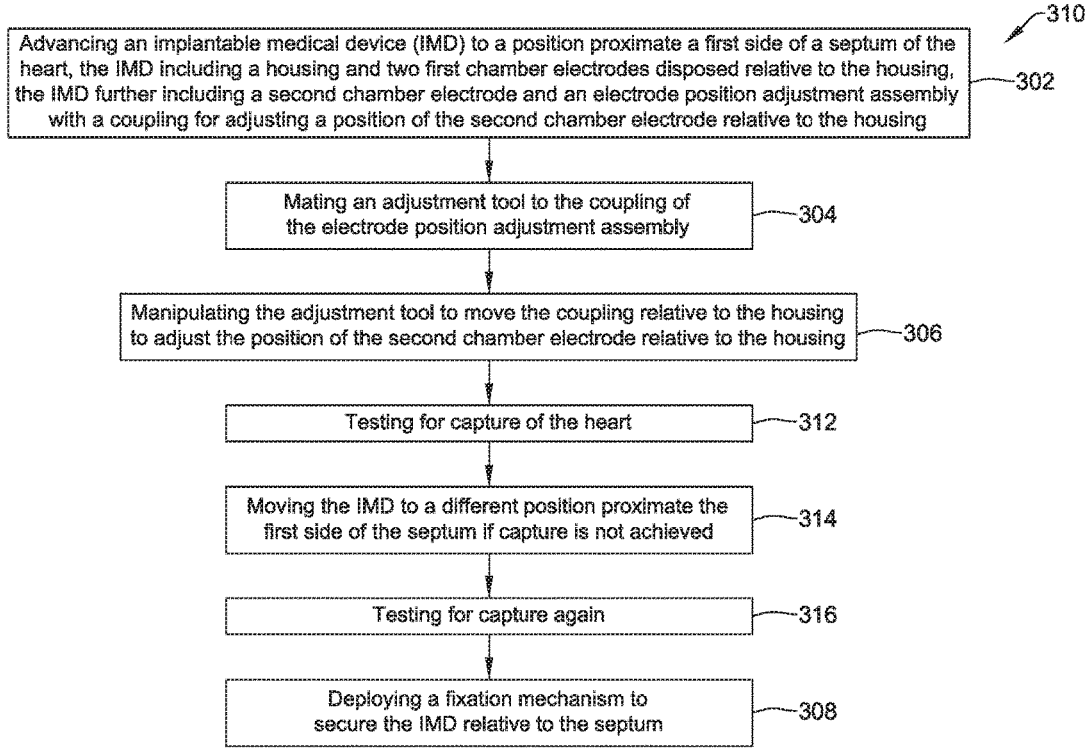
FIG. 12 is a flow diagram showing another illustrative method of facilitating dual chamber cardiac pacing.

FIG. 12 is a flow diagram showing an illustrative method 310 for facilitating dual chamber cardiac pacing. In some cases, and as shown at block 302, the method 300 includes advancing an IMD (such as but not limited to the IMD 20, the IMD 50 and/or the IMD 90) to a position proximate a first side of a septum of the heart, the IMD including a housing and two first chamber electrodes disposed relative to the housing, the IMD further including a second chamber electrode and an electrode position adjustment assembly with a coupling for adjusting a position of the second chamber electrode relative to the housing. As seen at block 304, an adjustment tool may be mated to the coupling of the electrode position adjustment assembly. The adjustment tool may be manipulated to move the coupling relative to the housing to adjust the position of the second chamber electrode relative to the housing as seen at block 306.

In some cases, and as indicated at block 312, the method 310 may include testing for capture of the heart. In some cases, the IMD may be at a good location for capture of the heart. In some cases, the initial placement may not yield good capture, and the IMD may be moved to a different position, as indicated at block 314. As shown at block 316, the method 310 may include testing again for capture. In some cases, this may be an iterative process. Once a location with good capture has been found, and as indicated at block 308, a fixation mechanism may be deployed to secure the IMD relative to the septum.

Figure 13:
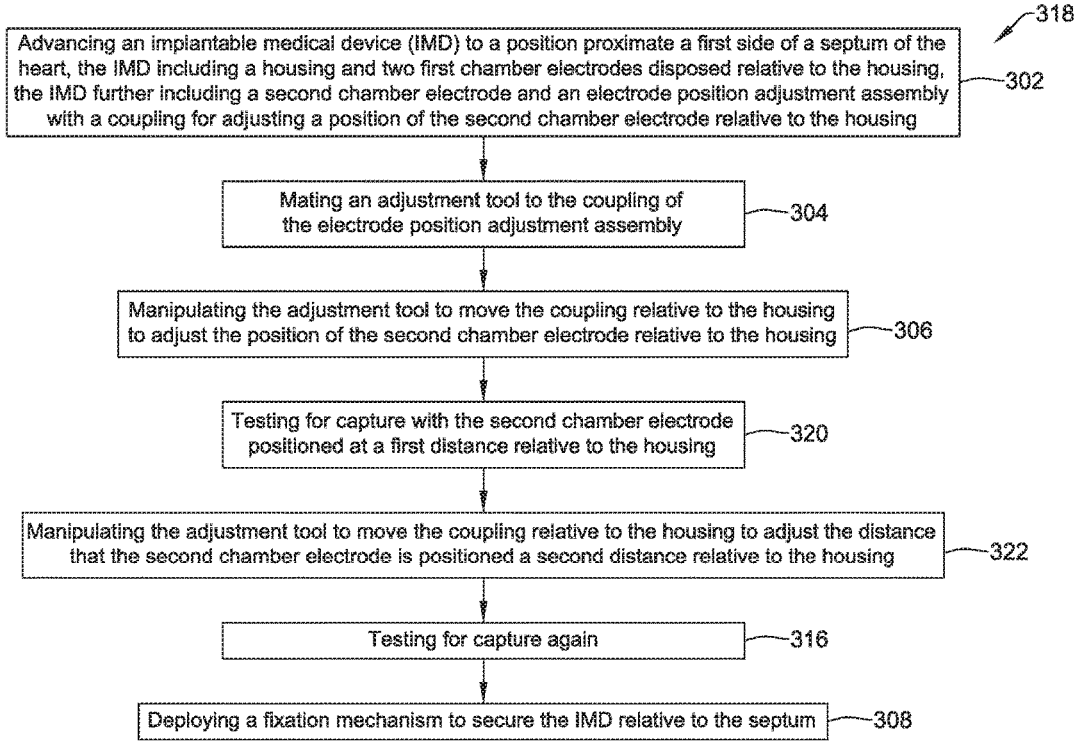
FIG. 13 is a flow diagram showing another illustrative method of facilitating dual chamber cardiac pacing.

FIG. 13 is a flow diagram showing an illustrative method 318 for facilitating dual chamber cardiac pacing. In some cases, and as shown at block 302, the method 300 includes advancing an IMD (such as but not limited to the IMD 20, the IMD 50 and/or the IMD 90) to a position proximate a first side of a septum of the heart, the IMD including a housing and two first chamber electrodes disposed relative to the housing, the IMD further including a second chamber electrode and an electrode position adjustment assembly with a coupling for adjusting a position of the second chamber electrode relative to the housing. As seen at block 304, an adjustment tool may be mated to the coupling of the electrode position adjustment assembly. The adjustment tool may be manipulated to move the coupling relative to the housing to adjust the position of the second chamber electrode relative to the housing as seen at block 306.

In some cases, and as indicated at block 320, the method 318 may include testing for capture of the heart with the second chamber electrode disposed at a first distance relative to the housing (alternatively, at a first penetration distance into the septum). In some cases, the electrode may be at a good depth for capture of the heart. In some cases, the initial depth may not yield good capture, and the electrode may be moved to a different position relative to the housing (or a different penetration depth), as indicated at block 322. As shown at block 324, the method 318 may include testing again for capture. In some cases, this may be an iterative process. Once a location with good capture has been found, and as indicated at block 308, a fixation mechanism may be deployed to secure the IMD relative to the septum.

In some cases, rather than extending or retracting a single electrode within the septum, the IMD may include a plurality of second chamber electrodes on the outer shaft being extended into the septum. In these cases, rather than moving a single electrode deeper into the septum, or partially withdrawing the single electrode from the septum, each of a series of individually addressable electrodes can be tested for capture.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments.

What is claimed is:

1. An implantable medical device (IMD) configured for deployment at a ventricular septum of a patient's heart, the ventricular septum of the patient's heart having a right ventricle (RV) facing side and a left ventricle (LV) facing side, the IMD comprising:
   a housing having a proximal end and a distal end, the housing configured to fit within the right ventricle (RV) of the patient's heart with the distal end of the housing proximate the RV facing side of the ventricular septum once the IMD is implanted in the patient's heart;
   a power source disposed within the housing;
   circuitry disposed within the housing and operatively coupled to the power source;
   a first RV electrode adjacent the distal end of the housing and positioned to be facing the RV facing side of the ventricular septum once the IMD is implanted, the first RV electrode operatively coupled with the circuitry in the housing;
   a second RV electrode spaced proximally of the first RV electrode, the second RV electrode operatively coupled with the circuitry in the housing;
   an LV electrode positioned distally of the first RV electrode and extends at least partially through the ventricular septum once the IMD is implanted, the LV electrode operatively coupled with the circuitry in the housing; and
   an LV electrode position adjustment assembly for adjusting a distance that the LV electrode is positioned distally of the first RV electrode, wherein the LV electrode position adjustment assembly comprises a coupling secured relative to the housing, wherein the coupling is configured to mate with a separate adjustment tool that can move the coupling relative to the housing to adjust the distance that the LV electrode is positioned distally of the first RV electrode.

2. The IMD of claim 1, wherein the LV electrode position adjustment assembly comprises a fixation helix extending distally from the housing, with the LV electrode positioned on the fixation helix, the fixation helix including a proximal shaft portion extending through a lumen of the housing and terminating in the coupling such that rotating the coupling rotates the fixation helix relative to the housing and causes the fixation helix to thread itself into the ventricular septum.

3. The IMD of claim 1, wherein the LV electrode position adjustment assembly comprises:
   an inner shaft operatively coupled to the coupling; and
   an outer shaft threadedly engaged with the inner shaft and configured to not rotate relative to the housing, wherein rotation of the inner shaft via the coupling results in translation of the outer shaft relative to the housing, wherein the LV electrode is secured relative to the outer shaft and translates with the outer shaft.

4. The IMD of claim 3, wherein at least a portion of the outer shaft has a cross-sectional profile that engages a complementary engagement portion of the housing to prevent rotation of the outer shaft relative to the housing.

5. The IMD of claim 4, wherein the cross-sectional profile comprises a non-circular cross-sectional profile and the complementary engagement portion of the housing comprises a distal opening in a lumen that receives at least part of the outer shaft.

6. The IMD of claim 3, wherein the coupling comprises a rotatable tether loop coupled to a proximal end of the inner shaft, such that rotating the rotatable tether loop rotates the inner shaft relative to the outer shaft, thereby causing the outer shaft to translate in response.

7. The IMD of claim 3, further comprising a spring contact disposed within the housing and operably coupled with the circuitry, the spring contact making sliding electrical contact with a portion of the outer shaft that is electrically coupled with the LV electrode.

8. The IMD of claim 1, further comprising one or more fixation tines that are configured to extend into the ventricular septum and curve over to anchor the IMD in place relative to the ventricular septum.

9. The IMD of claim 1, wherein the LV electrode serves as an antenna for communication purposes.

10. The IMD of claim 1, wherein the IMD comprises a dual chamber leadless cardiac pacemaker (LCP), and the LCP senses electrical activity on one side of the ventricular septum and delivers an actionable response on the other side of the ventricular septum.

11. An implantable medical device (IMD) configured for deployment within a heart chamber of a patient's heart, near a septum of the patient's heart, the septum of the patient's heart having a first chamber facing side facing the heart chamber and a second opposing chamber facing side, the IMD comprising:
   a housing configured to be positioned at least in part in the heart chamber proximate the first chamber facing side of the septum once the IMD is implanted in the patient's heart;
   a power source disposed within the housing;
   circuitry disposed within the housing and operatively coupled to the power source;
   one or more first chamber electrodes fixed relative to the housing and positioned to be proximate the first chamber facing side of the heart chamber once the IMD is implanted, the one or more first chamber electrodes operatively coupled with the circuitry in the housing;
   a lumen defined by the housing;
   an outer shaft that extends through the lumen and is translatable relative to the lumen;
   a second chamber electrode disposed at or near a distal end of the outer shaft, the second chamber electrode operably coupled with the circuitry disposed within the housing; and
   an inner shaft threadedly engaged with the outer shaft such that the inner shaft may be rotated relative to the outer shaft in order to effect translation of the outer shaft relative to the housing, the outer shaft translatable between a retracted position in which the second chamber electrode is proximate the first chamber facing side of the septum and an extended position in which the second chamber electrode extends at least partially into the septum.

12. The IMD of claim 11, wherein at least a portion of the outer shaft has a cross-sectional profile that engages a complementary engagement portion of the housing to prevent rotation of the outer shaft relative to the housing.

13. The IMD of claim 12, wherein the inner shaft extends proximally through the lumen and terminates in coupling such that rotating the coupling rotates the inner shaft relative to the outer shaft.

14. The IMD of claim 11, further comprising one or more fixation tines that are configured to extend into the septum and curve over to anchor the IMD in place relative to the septum.

15. The IMD of claim 11, further comprising a spring contact disposed within the housing and operably coupled with the circuitry, the spring contact making sliding electrical contact with a portion of the outer shaft that is electrically coupled with the second chamber electrode.

16. The IMD of claim 11, wherein the power source comprises a battery.

17. The IMD of claim 11, wherein the IMD comprises a dual chamber leadless cardiac pacemaker (LCP).

18. A method of facilitating dual chamber pacing of a heart, the method comprising:
- advancing a leadless cardiac pacemaker (LCP) to a position proximate a first side of a septum of the heart, the LCP including a housing and two first chamber electrodes disposed relative to the housing, the LCP further including a second chamber electrode and an electrode position adjustment assembly with a coupling for adjusting a position of the second chamber electrode relative to the housing;
- mating an adjustment tool to the coupling of the electrode position adjustment assembly;
- manipulating the adjustment tool to move the coupling relative to the housing to adjust the position of the second chamber electrode relative to the housing; and
- deploying a fixation mechanism to secure the LCP relative to the septum.

19. The method of claim 18, further comprising:
- testing for capture of the heart prior to deploying the fixation mechanism;
- moving the LCP to a different position proximate the first side of the septum if capture is not achieved; and
- testing for capture again.

20. The method of claim 18, further comprising:
- testing for capture with the second chamber electrode positioned at a first distance relative to the housing;
- manipulating the adjustment tool to move the coupling relative to the housing to adjust the distance that the second chamber electrode is positioned a second distance relative to the housing; and
- testing for capture again.

* * * * *